United States Patent [19]

Neustadt et al.

[11] Patent Number: 5,393,755
[45] Date of Patent: Feb. 28, 1995

[54] POLYCYCLIC GUANINE DERIVATIVES

[75] Inventors: Bernard R. Neustadt, West Orange; Neil A. Lindo, New Providence; Brian A. Mc Kittrick, Bloomfield, all of N.J.

[73] Assignee: Schering Corporation, Kenilworth, N.J.

[21] Appl. No.: 949,811

[22] PCT Filed: Jun. 20, 1991

[86] PCT No.: PCT/US91/04154

§ 371 Date: Dec. 14, 1992

§ 102(e) Date: Dec. 14, 1992

[87] PCT Pub. No.: WO91/19717

PCT Pub. Date: Dec. 26, 1991

Related U.S. Application Data

[63] Continuation-in-part of Ser. No. 541,568, Jun. 21, 1990, abandoned.

[51] Int. Cl.[6] .................... A61K 31/52; C07D 487/14
[52] U.S. Cl. .................... 514/233.2; 514/257; 514/267; 544/115; 544/230; 544/245; 544/247; 544/251; 544/252
[58] Field of Search ........... 544/251, 252, 115, 230, 544/245, 247; 514/267, 257, 233.2

[56] References Cited

U.S. PATENT DOCUMENTS

| | | | |
|---|---|---|---|
| 4,298,734 | 11/1981 | Temple, Jr. ................. | 544/251 |
| 5,064,947 | 11/1991 | Peet et al. .................... | 536/26 |
| 5,173,492 | 12/1992 | Suzuki et al. ................ | 514/267 |
| 5,270,316 | 12/1993 | Suzuki et al. ................ | 514/267 |

OTHER PUBLICATIONS

Nakanishi, et al., Journal of the American Chemical Society 92(26), 7617-7619, 30 Dec. 1970.
Alam, et al., Journal of Chromatography, vol. 499, pp. 571-578 (1990).

*Primary Examiner*—Mukund J. Shah
*Assistant Examiner*—Matthew G. Grumbling
*Attorney, Agent, or Firm*—Joseph T. Majka; Eric S. Dicker

[57] ABSTRACT

Novel polycylic guanine derivatives of the formula:

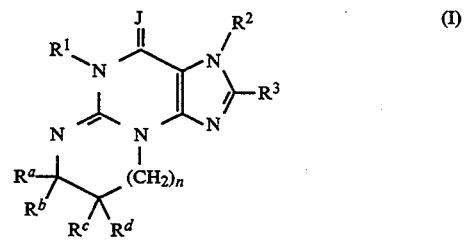

and

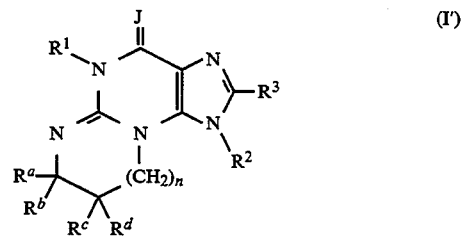

wherein J is oxygen or sulfur, $R^1$ is hydrogen, alkyl or alkyl substituted with aryl or hydroxy;

$R^2$ is hydrogen, aryl, heteroaryl, cycloalkyl, alkyl or alkyl substituted with aryl, heteroaryl, hydroxy, alkoxy, amino, monoalkyl amino or dialkylamino, or —$(CH_2)_m TCOR^{20}$ wherein m is an integer from 1 to 6, T is oxygen or —NH— and $R^{20}$ is hydrogen, aryl, heteroaryl, alkyl or alkyl substituted with aryl or heteroaryl;

$R^3$ is hydrogen, halo, trifluoromethyl, alkoxy, alkylthio, alkyl, cycloalkyl, aryl, aminosulfonyl, amino, monoalkylamino, dialkylamino, hydroxyalkylamino, aminoalkylamino, carboxy, alkoxycarbonyl or aminocarbonyl or alkyl substituted with awl, hydroxy, alkoxy, amino, monoalkylamino or dialkylamino;

$R^a$, $R^b$, $R^c$, and $R^d$ are defined in the specification; and n is zero or one.

The compounds of formulas (I) and (I') are useful as antihypertensive muscle relaxant and bronchodilating agents.

13 Claims, No Drawings

POLYCYCLIC GUANINE DERIVATIVES

The present application is the U.S. national application corresponding to International application Ser. No. PCT/US 91/04154, filed Jun. 20, 1991, and designating the United States, which PCT application is in turn a continuation-in-part of U.S. application Ser. No. 07/541,568, now abandoned, filed Jun. 21, 1990, the benefit of which applications are claimed pursuant to the provisions of 35 U.S.C. §§120,363 and 365(C).

BACKGROUND

The present invention relates to polycyclic guanine derivatives useful for treating cardiovascular and pulmonary disorders, as well as to their pharmaceutical compositions and methods for using the same.

SUMMARY OF THE INVENTION

The present invention is directed to novel polycyclic guanine derivatives of the formula:

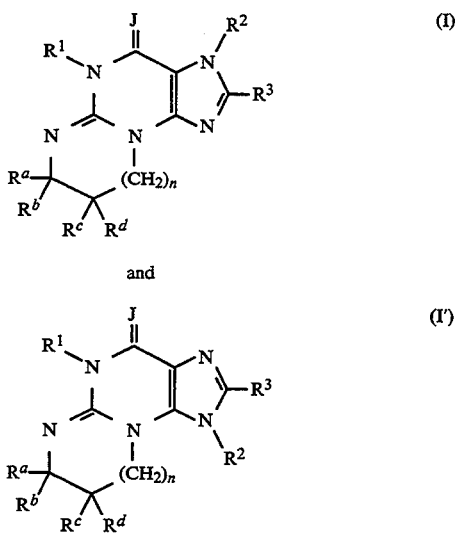

and wherein

J is oxygen or sulfur, $R^1$ is hydrogen, alkyl or alkyl substituted with aryl or hydroxy;

$R^2$ is hydrogen, aryl, heteroaryl, cycloalkyl, alkyl or alkyl substituted with aryl, heteroaryl, hydroxy, alkoxy, amino, monoalkyl amino or dialkylamino, or —(CH$_2$)$_m$TCOR$^{20}$ wherein m is an integer from 1 to 6, T is oxygen or —NH— and R$^{20}$ is hydrogen, aryl, heteroaryl, alkyl or alkyl substituted with aryl or heteroaryl;

$R^3$ is hydrogen, halo, trifluoromethyl, alkoxy, alkylthio, alkyl, cycloalkyl, aryl, aminosulfonyl, amino, monoalkylamino, dialkylamino, hydroxyalkylamino, aminoalkylamino, carboxy, alkoxycarbonyl or aminocarbonyl or alkyl substituted with aryl, hydroxy, alkoxy, amino, monoalkylamino or dialkylamino;

$R^a$, $R^b$, $R^c$ and $R^d$ independently represent hydrogen, alkyl, cycloalkyl or aryl; or ($R^a$ and $R^b$) or ($R^c$ and $R^d$) or ($R^b$ and $R^c$) can complete a saturated ring of 5- to 7-carbon atoms, or ($R^a$ and $R^b$) taken together and ($R^b$ and $R^c$) taken together, each complete a saturated ring of 5- to 7-carbon atoms, wherein each ring optionally can contain a sulfur or oxygen atom and whose carbon atoms may be optionally substituted with one or more or the following: alkenyl, alkynyl, hydroxy, carboxy, alkoxycarbonyl, alkyl or alkyl substituted with hydroxy, carboxy or alkoxycarbonyl; or such saturated ring can have two adjacent carbon atoms which are shared with an adjoining aryl ring; and n is zero or one.

Preferred compounds are those of formula (I). Preferably, J is O. Also preferred is that $R^1$ is alkyl, more preferably methyl. For $R^2$, preferred substituents include hydrogen, benzyl, 4-chlorobenzyl, cyclohexylmethyl and trimethylacetoxymethyl. For $R^3$, preferred substituents include hydrogen and alkyl such as methyl or ethyl. Preferably n is zero. Also preferred is that ($R^a$ and $R^b$) form a saturated 5 membered ring, that ($R^b$ and $R^c$) form a saturated 5, 6 or 7 membered ring or ($R^a$ and $R^b$) and ($R^b$ and $R^c$) each can complete a saturated ring and each ring contains 5 or 6 carbon atoms. When ($R^b$ and $R^c$) form a saturated 5, 6 or 7 membered ring, generally the preferred stereochemistry is (R) at the carbon atom bearing $R^b$ and the preferred stereochemistry is (S) at the carbon atom bearing $R^c$.

The compounds of formulas (I) and (I') are useful as antihypertensive, bronchodilating and blood platelet inhibiting agents. Compounds (I) and (I') are also useful in inhibiting phosphodiesterase enzymes. The inhibition of vascular phosphodiesterase is believed to induce antihypertensive activity. Compounds (I) and (I') can also serve as smooth muscle relaxants and are therefore useful in the treatment of bronchoconstriction. Such compounds also can inhibit platelet function and are useful in treating conditions benefitting from inhibiting platelet function.

The present invention is also directed toward a pharmaceutical composition containing at least one of compounds (I) and (I') in an amount effective to inhibit phosphodiesterase or relax smooth muscle. The present invention is also directed toward a pharmaceutical composition containing an anti-hypertensive, a bronchodilating or a platelet inhibiting effective amount of the compounds (I) and (I').

The present invention is also directed toward a method for treating hypertension, bronchoconstriction or diseases benefitting from platelet inhibition in a mammal comprising administering to a mammal in need of such treatment an amount of at least one of compounds (I) and (I') effective to treat any of the above diseases. The present invention is also directed toward a method for maintaining guanosine 3':5'-cyclic monophosphate (cGMP) levels in a mammal by administering an amount of compounds (I) and (I') effective to maintain or increase cGMP levels.

DETAILED DESCRIPTION OF THE INVENTION alkyl—represents a straight chain saturated hydrocarbon moiety having from 1 to 10, preferably from 1 to 6 carbon atoms or a branched hydrocarbon moiety of 3 to 10 carbon atoms, preferably from 3 to 6, such as for example methyl, ethyl, propyl, isopropyl, butyl, isobutyl, tert-butyl, pentyl, hexyl, decyl and the like;

alkoxy—represents an alkyl moiety as defined above covalently bonded to an oxygen atom, as for example, methoxy, ethoxy, propoxy, pentyloxy, hexyloxy, decyloxy and the like;

alkenyl—represents a straight chain hydrocarbon chain hydrocarbon moiety of two to 10 carbon atoms or a branched hydrocarbon moiety of three to 10 carbon atoms having at least one carbon-to-carbon double bond such as ethenyl, 1-propenyl, 1-butenyl, 2-butenyl, isobutenyl, 1-pentenyl, 2-methyl-1-butenyl, 1-hexenyl and the like;

alkynyl—represents a straight chain hydrocarbon moiety of two to 10 carbon atoms or a or branched hydrocarbon chain of four to 10 carbon atoms having at least one carbon to carbon triple bond such as for example ethynyl, 1-propynyl, 1-butynyl, 1-pentynyl, 2-pentynyl, 1-hexynyl, 2-hexynyl, 3-hexynyl and the like;

alkylthio—represents an alkyl moiety as defined above bonded to a sulfur atom;

aryl—represents a carbocyclic moiety containing at least one benzenoid-type ring, with the aryl moiety having from 6 to 14 carbon atoms, with all available substitutable carbon atoms of the aryl moiety being intended as possible points of attachment, for example phenyl, naphthyl, indenyl, indanyl and the like, and wherein said carbocyclic moiety can be optionally substituted with one to three moieties independently selected from the following: halo, alkyl, trifluoromethyl, phenyl, hydroxy, alkoxy, phenoxy, amino, monoalkylamino or dialkylamino;

cycloalkyl—represents a saturated carbocyclic ring containing from 3 to 7 carbon atoms, such as for example, cyclopropyl, cyclobutyl, cyclopentyl, cyclohexyl and the like;

halo—represents fluoro, chloro, bromo or iodo;

heteroaryl—represents a cyclic group having at least one O, S and/or N interrupting a carbocyclic ring structure and having a sufficient number of delocalized pi electrons to provide aromatic character, with the aromatic heterocyclic group having from 2 to 14, preferably from 2 to 6 carbon atoms, for example 2-, 3- or 4-pyridyl, 2- or 3-furyl, 2- or 3-thienyl, 2-, 4- or 5-thiazolyl, 1, 2-, 4- or 5-imidazolyl, 2-, 4-or 5-pyrimidinyl, 2-pyrazinyl, 3- or 4-pyridazinyl, 3-, 5- or 6-[1,2,4-triazinyl], 3- or 5-[1,2,4-thiadazolyl], 2-, 3-, 4-, 5-, 6- or 7-benzofuranyl, 1-, 2-, 3-, 4-, 5-, 6- or 7-indolyl, 1-, 3-, 4- or 5-pyrazolyl, 2-, 4- or 5-oxazolyl and the like;

aminosulfonyl—a sulfonyl moiety bonded to an amino or alkylamino moiety of one to six carbon atoms, e.g. —SO$_2$NH$_2$, —SO$_2$NHCH$_3$, —SO$_2$N(CH$_3$)$_2$ and the like.;

monoalkylamino—an amino moiety in which one of the hydrogens has been substituted with an alkyl moiety as defined hereinbefore;

dialkylamino—an amino moiety in which each of the hydrogens has been substituted independently with an alkyl moiety;

Certain compounds of the invention e.g., those with a basic nitrogen containing moiety, can also form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner.

Certain compounds of the invention will be acidic in nature, e.g., those compounds which possess a carboxy or phenolic hydroxyl group. These compounds may form pharmaceutically acceptable salts. Examples of such salts are the sodium, potassium, calcium, aluminum, gold and silver salts. Also contemplated are salts formed with pharmaceutically acceptable amines such as ammonia, alkylamines, hydroxyalkylamines, N-methylglucamine and the like.

The compounds of the present invention can be prepared by several preparative routes as described hereinafter. Variations of these routes can be employed, as well as other routes known to those skilled in the art such as those described in the various references cited throughout the specification, whose preparative teachings are incoporated herein by reference.

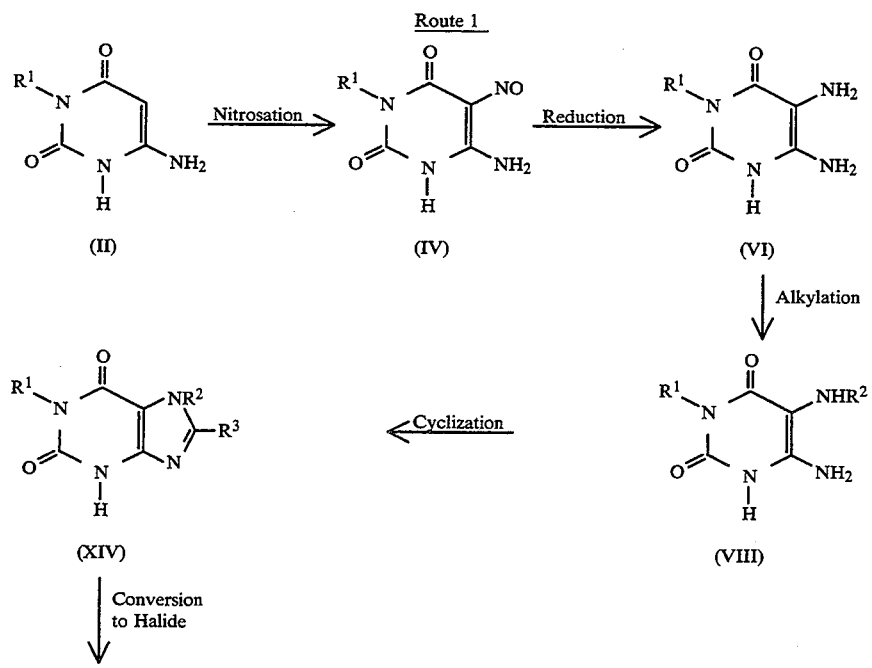

Route 1

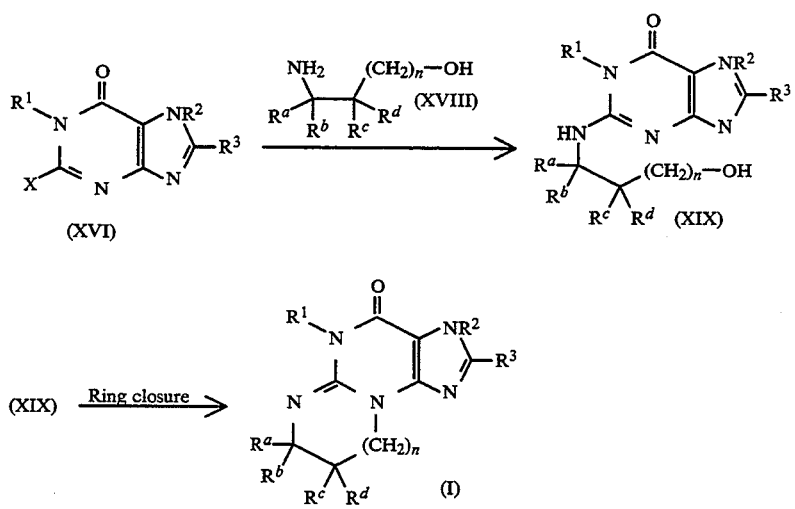

In Route 1, the compounds of formula (IV) can be prepared by contacting compound (II) with a nitrosating agent such as nitrous acid, as described in Arnold Weissberger (ed.), The Chemistry of Heterocyclic Compounds, A Series of Monographs, The Pyrimidines, Interscience Publishers, John Wiley & Sons, New York (1962), whose preparative teachings are incorporated herein by reference.

The compounds of formula (VI) can be prepared by contacting compound (IV) with a reducing agent such as hydrogen with a catalyst, a metal with an acid, or a sulfur containing reducing agent such as sodium dithionite, as described in Weissberger, supra.

The compounds of formula (VIII) can be prepared by reductive alkylation of compounds (VI) entailing contacting compound (VI) with a carbonyl compound and reducing the intermediate thus obtained by catalytic hydrogenation as described hereinbefore or by reduction with a hydride reducing agent such as sodium cyanoborohydride, as described in Mary Fieser and Louis Fieser, Reagents for Organic Synthesis, Vol. 1-13, John Wiley & Sons, New York (1979-88), whose preparative teachings are incorporated herein by reference.

The compounds of formula (XIV) can be prepared by cyclizing the adduct prepared from compound (VIII) with a carboxylic acid derivative such as an orthoester of the formula $R_3C(OCH_3)_3$ as taught in Weissberger, The Chemistry of Heterocyclic Compounds, A Series of Monographs, The Fused Pyrimidines, Vol. 2, Purines, Interscience Publishers, John Wiley & Sons, New York (1967).

The compounds of formula (XVI) wherein X is Cl or Br can be prepared by converting compounds (XIV) to their halide form with a halide forming reagent such as phosphorus oxychloride ($POCl_3$) as taught in Weissberger, The Fused Pyrimidines, supra.

The compounds of formula (XIX) can be prepared by amination of compounds (XVI) with aminoalcohol (XVIII) optionally in the presence of a suitable acid acceptor such as triethylamine, according to known or analogous procedures such as taught in Weissberger, The Fused Pyrimidines, supra. A particularly useful method employs excess diisopropylethylamine in a solvent such as N-methylpyrrolidinone at elevated temperatures of 100° to 150° C.

The desired compounds of formula (I) can be prepared by ring closure of compound (XIX) with a suitable dehydrating agent such as thionyl chloride or triphenylphosphine dibromide according to known or analogous procedures as taught in Fieser and Fieser, supra.

The compounds of formula (I) and (I') wherein $R^1$ or $R^2$ is benzyl or substituted benzyl can be converted to the corresponding intermediate compounds (I) and (I') wherein $R^1$ or $R^2$ is hydrogen by hydrogenolysis, as for example, with hydrogen and palladium catalyst. The corresponding intermediate compounds (I) and (I') wherein $R^1$ or $R^2$ is hydrogen can then be convened to compounds (I) and (I') wherein $R^1$ or $R^2$ represents the non-hydrogen substituents for $R^1$ and $R^2$, with an alkylating agent $R^1Y$ or $R^2Y$, wherein Y is a leaving group, e.g., halo or sulfonate such as mesylate or triflate, in the presence of a suitable base.

Routes 2 and 3

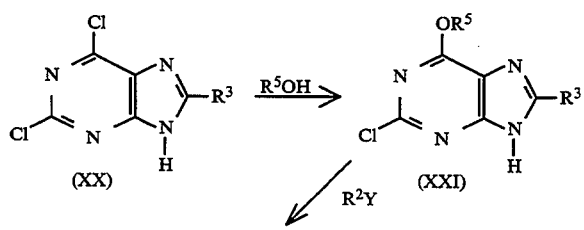

-continued

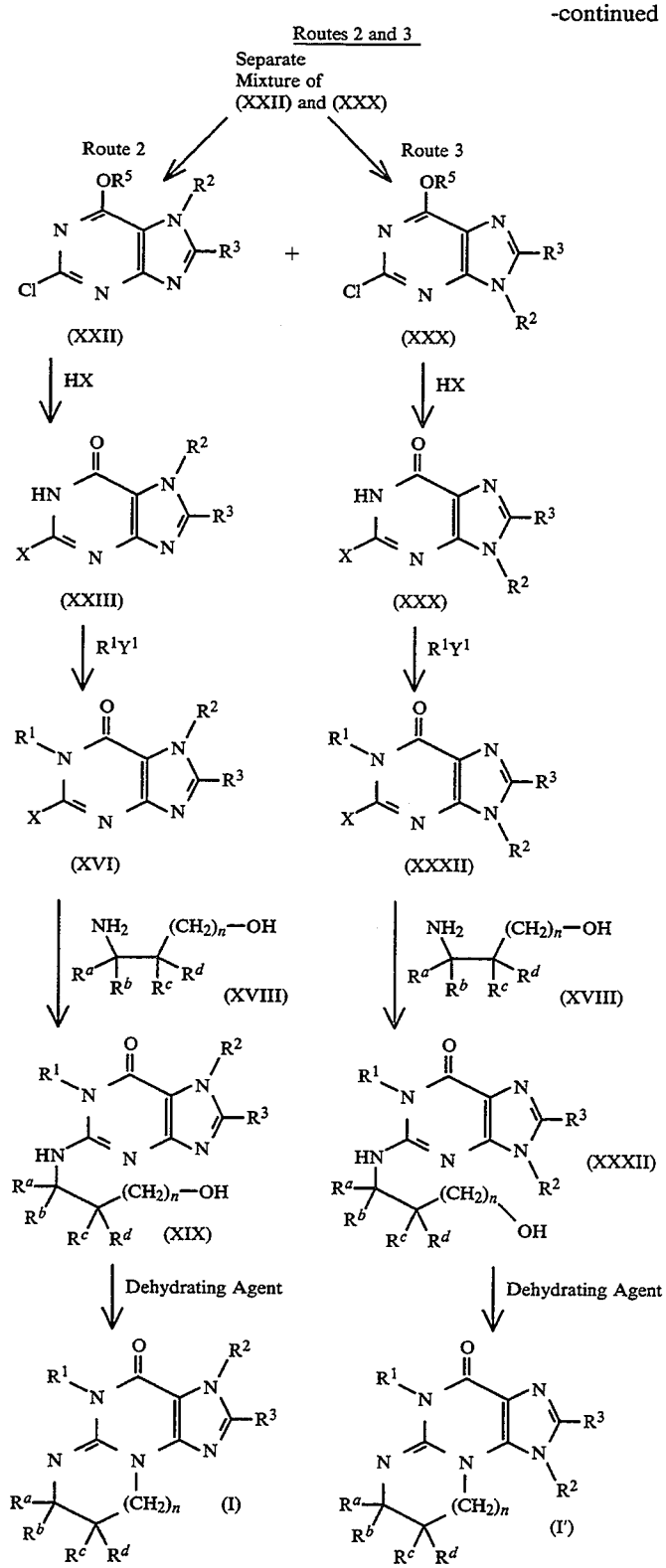

In Routes 2 and 3, compound (XXI) can be prepared by contacting the 2,6-dichloropurine compound (XX) with a benzylic alcohol of the formula $R^5OH$, wherein $R^5$ represents benzyl or substituted benzyl, in the presence of a suitable base such as sodium hydride (NaH) in a solvent such as DMF or THF. Compound (XXI) is contacted with a compound of the formula $R^2Y$ wherein $R^2$ and Y are as defined hereinbefore in the presence of a base such as potassium carbonate ($K_2CO_3$) and a solvent such as dimethylformamide (DMF) to give a mixture containing monochlorinated purines (XXII) and (XXX). These compounds are then separated by conventional procedures, such as chromatography or crystallization.

In Route 2, compound (XXII) can be contacted with an acid such as HX wherein X is chloro or bromo in an organic acid such as acetic acid to give the compound (XXIII). Compound (XXIII) can then be contacted with a compound of formula $R^1Y^1$ wherein $R^1$ is defined hereinbefore and $Y^1$ is a leaving group representing any of the values for Y, in the presence of a base such as lithium hydroxide in dimethylformamide, as described in D. Ranganathan and F. Farooqui, Tet. Lett. 25, 5701 (1984) to give compound (XVI). Compound (XVI) can be converted to the desired compound (I) as described in Route 1. Similarly, in Route 3, desired compounds (I') can be prepared according to the procedures as described in Routes 1 and 2.

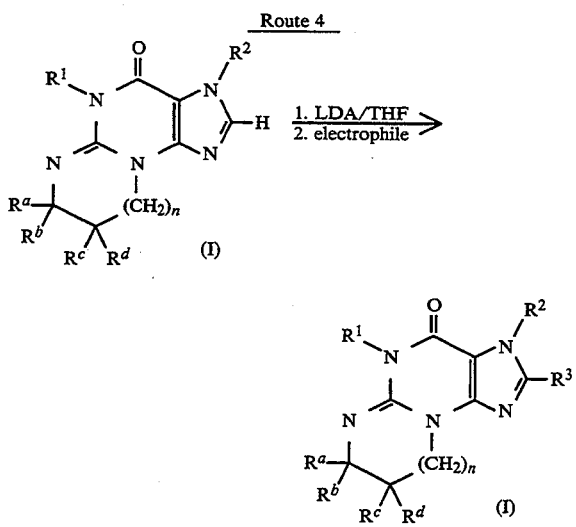

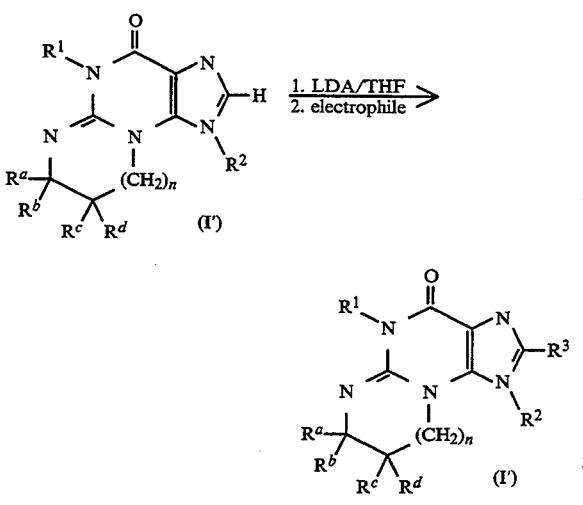

In Route 4, the compounds of formula (I) or (I') wherein $R^3$ is alkyl, halo, alkylthio, carboxy or alkoxycarbonyl, can be prepared by, in step 1, contacting compound (I) or (I') wherein $R^3$ is hydrogen, with a base such as lithium diisopropylamide (LDA) in a suitable solvent such as THF. In step 2, the adduct from step 1 is treated with a corresponding electrophile giving $R^3$, such as halogen, e.g. $Br_2$ giving $R^3$=Br, a disulfide, e.g. $CH_3SSCH_3$ giving $R^3$=$CH_3S$, carbon dioxide ($CO_2$) giving $R^3$=COOH, methyl iodide ($CH_3I$) giving $R^3$=$CH_3$, and the like. See H. Hayakawa, K. Haraguchi, H. Tanaka and T. Miyasaka, Chem. Pharm. Bull., 35( 1), pp. 72–79 (1987) for analogous procedures. The compounds of formula (I) wherein $R^3$ is amino, monoalkylamino, dialkylamino, alkylthio or alkoxy can be prepared by contacting a compound of formula (I) wherein $R^3$ is halogen with an amine, alkyl mercaptide or alkoxide to form the corresponding amino, alkylthio or alkoxy compound (I) as taught in Weissberger, The Fused Pyrimidines, supra.

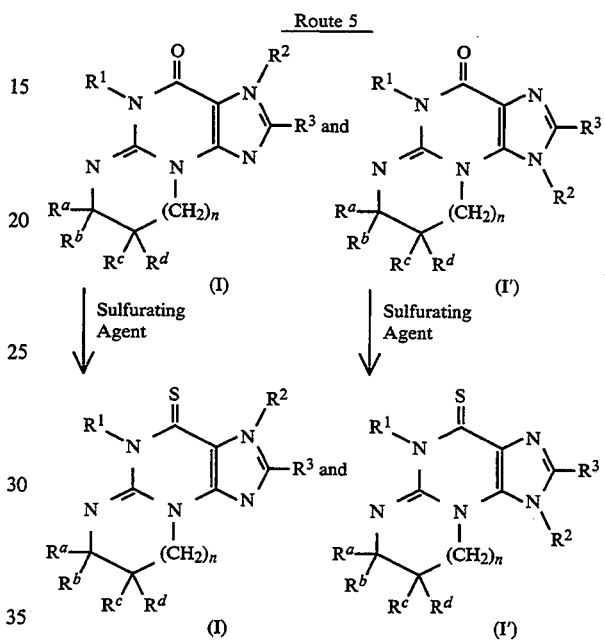

In Route 5, the sulfur containing compounds (I), and (I') wherein J=S, can be prepared by contacting the oxygen containing compounds (I) and (I') wherein J=O, with a sulfurating agent such as phosphorus pentasulfide ($P_2S_5$), or Lawesson's reagent, as taught in J. March, Advanced Organic Chemistry, Reactions, Mechanisms and Structure, 3rd Edition, John Wiley & Sons, New York, (1985), pp. 793–795, whose preparative teachings are incorporated here by reference.

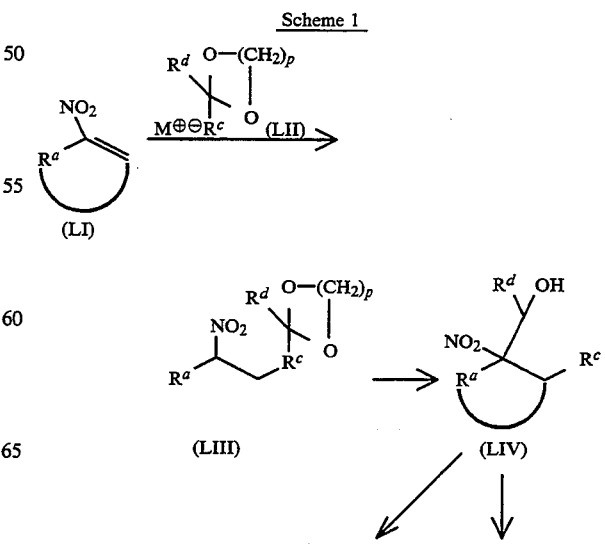

-continued
Scheme 1

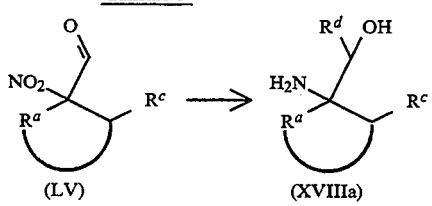

Aminoalcohols (XVIII) are known or may be prepared by known methods, such as taught in Rodd's Chemistry of Carbon Compounds, 2nd Edition, Vol. 1, Part D., pp 34–37, whose preparative teachings are incoporated herein by reference.

Compounds (XVIIIa) represent the case where ($R^a$ and $R^b$) and ($R^b$ and $R^c$) each complete a saturated ring, $R^b$ is CH, and n is 0. These may be prepared according to Scheme 1, where p is 2 or 3, and $R^a$, $R^c$, and $R^d$ are as defined hereinbefore. Compound (LIII) can be prepared by treating compound (LI) with an organometallic reagent (LII), i.e. grignard reagent or a zinc copper reagent as described in E. J. Corey et al., Journal of American Chemical Society, 1978 page 6294 or P. Knochel et al., Journal of Organic Chemistry, 1989, pg. 5200, whose preparative teachings are incorporated herein by reference.

Compound (LIV) can be prepared by treating compound (LIII) with a protic acid in alcohol, e.g. toluenesulfonic acid or hydrochloric acid in methanol, at refluxing temperatures, followed by treatment with an aqueous solution of a protic acid in a solvent such as hydrochloric acid in THF. Subsequent treatment with a base, e.g. potassium carbonate in an alcoholic solvent such as methanol, gives compound (LIV).

Compound (XVIIIa) can be prepared by treating compound (LIV) with a reducing agent, e.g. by hydrogenation with Raney nickel or reduction with sodium borohydride in an alcohol solvent, e.g methanol. Alternatively, when $R^d$ is H, compound (XVIIIa) can be prepared by treating compound (LIV) with an oxidizing agent such as pyridinium chlorochromate (PCC) to give ketone (LV), followed by reduction with a reducing agent such as borohydride in an alcoholic solvent, followed by hydrogenation with a suitable catalyst, e.g. Raney nickel, to give the desired compound (XVIIIa).

The following examples are presented to illustrate typical compounds of the present invention, but the scope of the invention is not to be considered limited to such examples.

EXAMPLE 1 cis-5,6a,7,8,9,9a-Hexahydro-5-methyl-3-(phenylmethyl)cyclopent[4,5]imidazo[2,1-b]purin-4-one

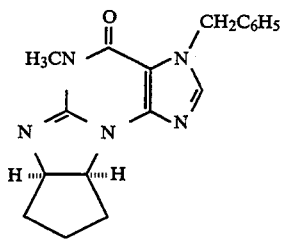

Add 3.2 g SOCl₂ (27 mmol) to a solution of 2-(trans-2-hydroxycyclopentylamino)-1-methyl-7-(phenylmethyl)purin-6-one (3.0 g=8.8 mmol) in 150 ml CH₂Cl₂. Stir the solution overnight, wash with cold 2N NaOH, dry, and solvent strip. Chromatograph the residue on silica (98:2 CH₂Cl₂/CH₃OH) to give the title compound as a foamed solid, FAB MS: M+1=322.

EXAMPLE 2

7,8-Dihydro-5-methyl-3-(phenylmethyl)-3H-imidazo[2,1-b]purin-4(5H)-one: white solid, EI MS: M+=281.

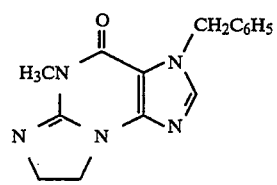

By using 2-(2-hydroxyethylamino)-1-methyl-7-(phenylmethyl)purin-6-one in accordance with Example 1, the title compound is obtained.

EXAMPLE 3 cis-6a,7,8,9,10,10a-Hexahydro-5-methyl-3-(phenylmethyl)-3H-benzimidazo[2,1-b]purin-4(5H)-one: white foam, EI MS: M+=335

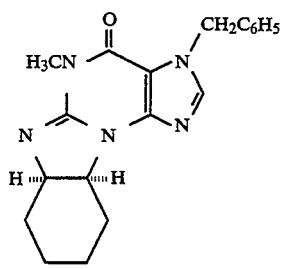

By using 2-(trans-2-hydroxycyclohexylamino)-1-methyl-7-(phenylmethyl)purin-6-one in accordance with Example 1, the title compound is obtained.

EXAMPLE 4

5,7,8,9-Tetrahydro-5-methyl-3(phenylmethyl)-pyrimido[2,1-b]purin-4(3H)-one, hydrochloride: white solid, FAB MS: M-HCl=295

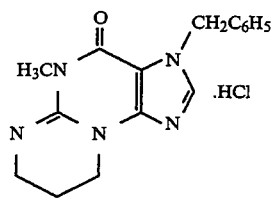

By using 2-(3-hydroxypropylamino)-1-methyl-7-(phenylmethyl)purin-6-one in accordance with Example 1, the title compound is obtained.

EXAMPLE 5

7,8-Dihydro-8-phenyl-5-methyl-3-(phenylmethyl)-3H-imidazo[2,1-b]purin-4(5H)-one: colorless gum, FAB MS: M+1=358.

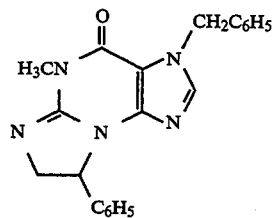

By using 2-(2-hydroxy-2-phenylethylamino)-1-methyl-7-(phenylmethyl)purin-6-one in accordance with Example 1, the title compound is obtained.

EXAMPLE 6

5',7'-Dihydro-5'-methyl-3-(phenylmethyl)spiro[cyclohexane-1,8'-(8H)-imidazo[2,1-b]purin]-4'(3'H)one: white solid, CI MS: M+1=350.

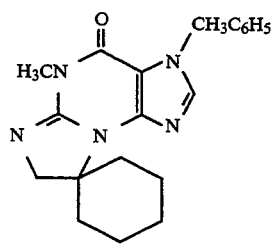

By using 2-(1-(hydroxycyclohexyl)methylamino)-1-methyl-7-(phenylmethyl)purin-6-one in accordance with Example 1, the title compound is obtained.

EXAMPLE 7 cis-5,6a,11,11a-Tetrahydro-5-methyl-3-(phenylmethyl)indeno[1',2':4,5]imidazo[2,1-b]purin-4(3H)-one: foamed solid, CI MS: M+1=374.

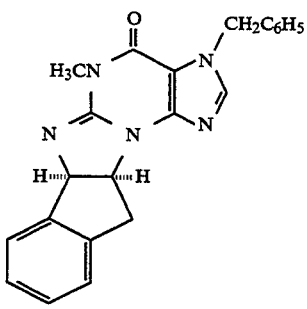

By using 2-(2-hydroxy-1-indanylamino)-1-methyl-7-(phenylmethyl)purin-6-one in accordance with Example 1, the title compound is obtained.

By use of the appropriate amino-alcohol in accordance with Example 1, the following compounds are obtained:

7A8 5',7'-Dihydro-2',5'dimethyl-3'-(phenylmethyl)-spiro{cyclohexane-1,7'-(8'H)-imidazo[2,1-b]purin}-4'(3'H)-one: off-white solid, EI MS: M+ =363.

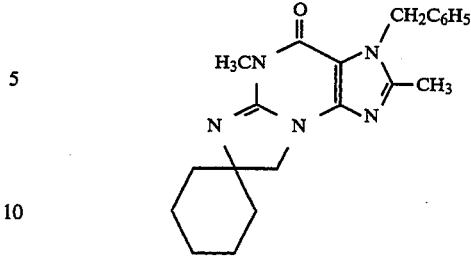

7A9 7,8-Dihydro-2,5,7,7,8(R,S)-pentamethyl-3H-imidazo[2,1-b]purin-4(5H)-one: white solid, EI MS: M+ =247.

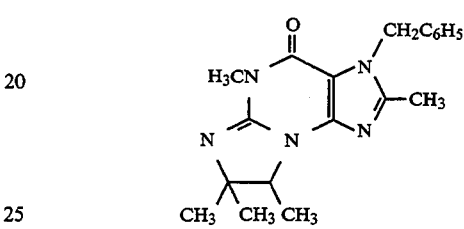

EXAMPLE 8 cis-5,6a,7,11 b-Tetrahydro-5-methyl-3-(phenylmethyl)indeno[2',1';4,5]imidazo[2,1-b]purin-4(3H)-one: white solid, CI MS: M+1=370.

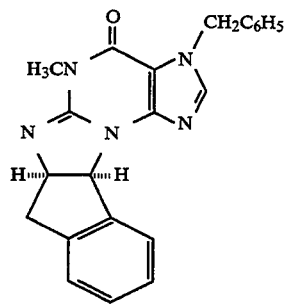

By using 2-(1-hydroxy-2-indanylamino)-1-methyl-7-(phenylmethyl)purin-6-one in accordance with Example 1, the title compound is obtained.

EXAMPLE 9 cis-5,6a,7,8,9,9a-Hexahydro-2,5-dimethyl-3-(phenylmethyl)cyclopent[4,5]imidazo[2,1-b]purin-4-(3H)-one: off-white solid, CI MS: M+1=336.

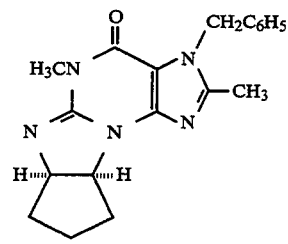

By using 2-(trans-2-hydroxycyclopentylamino)-1,8-dimethyl-7-(phenylmethyl)purin-6-one in accordance with Example 1, the title compound is obtained.

By use of the appropriate amino-alcohol in accordance with Example 1, the following compounds are obtained:

9A3  5'-methyl-3'-(phenylmethyl)-spiro[cyclopentane-1,7-(8'H)-(3'H)-imidazo[2,1-b]purin]-4-(5'H)-one: off-white solid, CI MS: M+1=336.

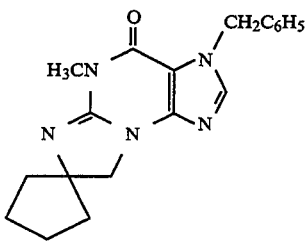

9A4. 7,8-Dihydro-2,5,7,7-tetramethyl-3-(phenylmethyl)-3H-imidazo[2,1-b]purin-4(5'H)-one: white foamed solid, CI MS: M+1=324.

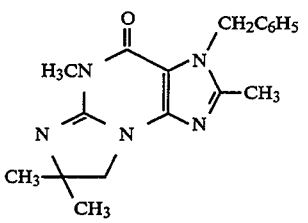

9A5  7,8-Dihydro-7(R)-phenyl-2,5-dimethyl-3-(phenylmethyl)-3H-imidazo[2,1-b]purin-4(5H)-one: off-white solid, CI MS: M+1=372. $[\alpha]_D^{26}=+44.4°$.

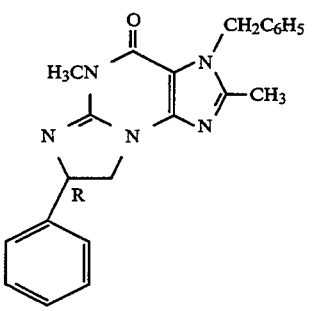

9A6  7,8-Dihydro-2,5-dimethyl-3,7(R)-bis(phenylmethyl)-3H-imidazo[2,1-b]purin-4(5H)-one: tan solid, EI MS: M+=385. $[\alpha]_D^{23.5}=+11.6°$.

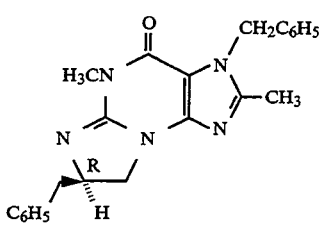

9A7  (±)-7,8-Dihydro-2,5-dimethyl-7-ethyl-3-(phenylmethyl)-3H-imidazo[2,1-b]purin-4(5H)-one: tan solid, CI MS: M+1=324.

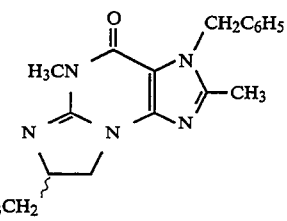

9A8  6a(S)-7,8,9,10,10a(R)-hexhydro-2,5-dimethyl-3-(phenylmethyl)-3H-benzimidazo[2,1-b]purin-4(5H)-one: tan foam, CI MS: M+1=350, $[\alpha]_D^{26}=-79.1°$.

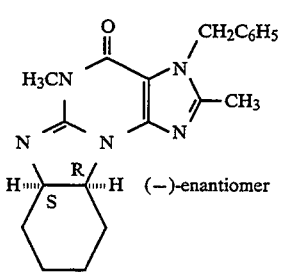

9A9  6a(R)-7,8,9,10,10a(S)-hexahydro-2,5-dimethyl-3-(phenylmethyl)-3H-benzimidazo[2,1-b]purin-4(5H)-one: off-white foamed solid, CI MS: M+1=350, $[\alpha]_D^{26}=+83.0°$.

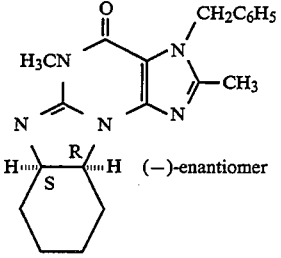

9A10  7,8-Dihydro-2,5-dimethyl-7(R)-isopropyl-3-(phenylmethyl)-3H-imidazo[2,1-b]purin-4(5H)-one: tan solid, CI MS: M+1=338, $[\alpha]_D^{26}=+64.8°$.

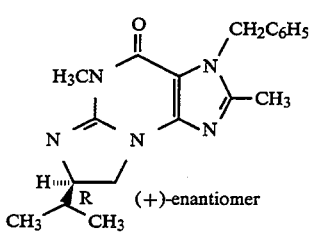

9A11  7,8-Dihydro-2,5,7(R)-trimethyl-3-(phenylmethyl)-3H-imidazo[2,1-b]purin-4(5H)-one: white solid, CI MS: M+1=310, $[\alpha]_D^{26}=+79.4°$.

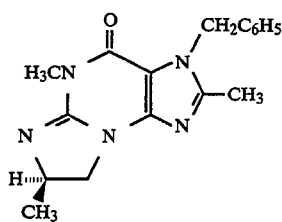

9A12 cis-7,7a,8,9,10,10a-Hexahydro-2,5-dimethyl-3-(phenylmethyl)-3H-cyclopenta[5,6]pyrimido[2,1-b]purin-4(5H)-one: tan foamed solid, CI MS: M+1=350.

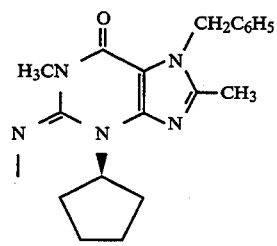

9A13 7,8-Dihydro-2,5-dimethyl-7(S)-(1-methylpropyl)-3-(phenylmethyl)-3H-imidazo[2,1-b]purin-4(5H)-one: crystalline solid, FAB MS: M+1=352, $[\alpha]_D^{24} = -60.8°$.

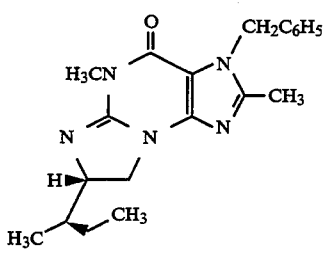

9A14 7,8-Dihydro-2,5-dimethyl-7(R)-(2-methylpropyl)-3-(phenylmethyl)-3H-imidazo[2,1-b]purin-4(5H)-one: clear gum, CI MS: M+1=352., $[\alpha]_D^{24} = +73.1°$.

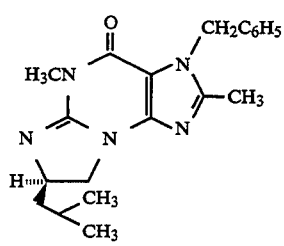

9A15 7,8-Dihydro-2,5-dimethyl-7(R,S)-(methoxycarbonyl)-3(phenylmethyl)-3H-imidazo[2,1-b]purin-4(5H)-one: tan foam, FAB MS: M+1=354.

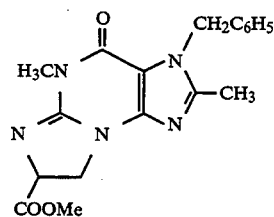

9A16 7,8-Dihydro-2,5-dimethyl-7(R,S)-(1-propyl)-3-(phenylmethyl)-3H-imidazo[2,1-b]purin-4(5H)-one: tan solid, CI MS: M+1=338.

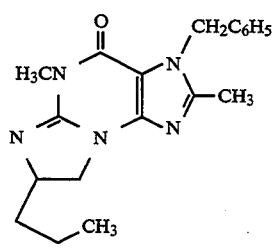

9A17 7,8-Dihydro-2,5-dimethyl-7(S)-(1-methylethyl)-3-(phenylmethyl)-3H-imidazo[2,1-b]purin-4(5H)-one: white foamed solid, CI MS: M+1=338, $[\alpha]_D^{23.5} = -65.6°$.

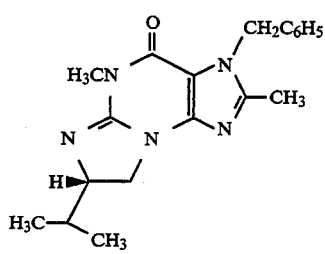

9A18 7,8-Dihydro-2,5,7,7,8(R,S)-pentamethyl-3-(phenylmethyl)-3H-imidazo[2,1-b]purin-4(5H)-one: off-white solid, EI MS: M+=337.

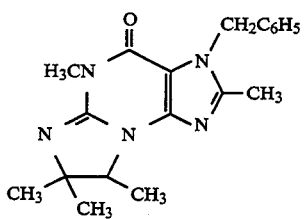

9A19: 5,7,8,9-Tetrahydro-2,5,7,9(R,S)-pentamethyl-3-(phenylmethyl)-pyrimido[2,1-b]purin-4(3H)-one: white solid, EI MS: M+=351.

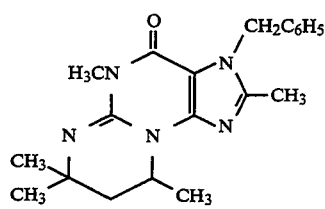

EXAMPLE 10

5,6a(R),7,8,9,9a(S)-Hexahydro-2,5-dimethyl-3-(phenylmethyl)cyclopent[4,5]imidazo[2,1-b]purin-4(3H)-one: white solid, CI MS: M+1=336, $[\alpha]_D^{26}= +122.4°$.

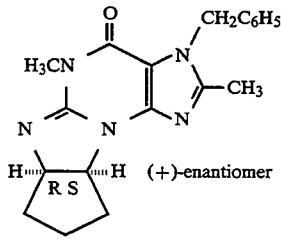

(+)-enantiomer

By using 2-(2(R)-hydroxy-1(R)-cyclopentylamino)-1,8-dimethyl-7-(phenylmethyl)purin-6-one in accordance with Example 1, the title compound is obtained.

EXAMPLE 11

5,6a(S),7,8,9,9a(R)-Hexahydro-2,5-dimethyl-3-(phenylmethyl)cyclopent[4,5]imidazo[2,1-b]purin-4(3H)-one: white solid, CI MS: M+1=336, $[\alpha]_D^{26}= -122.4°$.

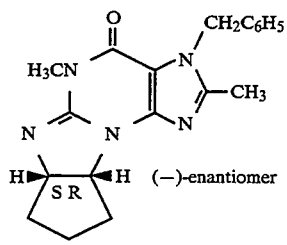

(−)-enantiomer

By using 2-(2(S)-hydroxy-1(S)-cyclopentylamino)-1,8-dimethyl-7-(phenylmethyl)purin-6-one in accordance with Example 1, the title compound is obtained.

EXAMPLE 12 cis-6a,7,8,9,10,10a-Hexahydro-2,5-dimethyl-3-(phenylmethyl)-3H-benzimidazo[2,1-b]purin-4(5H)-one: white solid, CI MS: M+1=350.

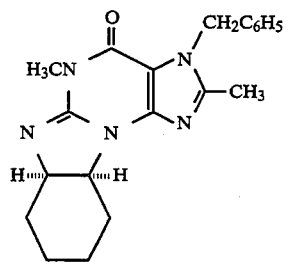

By using 2-(trans-2-hydroxycyclohexylamino)-1,8-dimethyl-7-(phenylmethyl)purin-6-one in accordance with Example 1, the title compound is obtained.

EXAMPLE 13

5',7'-Dihydro-2',5'-dimethyl-3'-(phenylmethyl)spiro[cyclohexane-1,8'-(8H)-imidazo[2,1-b]purin]-4'(3'H)-one: tan foamed solid, CI MS: M+1=364.

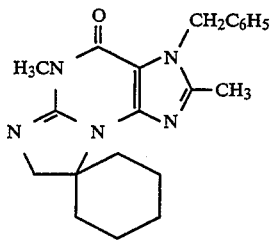

By using 2-(1-(hydroxycyclohexyl)methylamino)-1,8-dimethyl-7-(phenylmethyl)purin-6-one in accordance with Example 1, the title compound is obtained.

EXAMPLE 14 cis-5,6a,7,8,9,9a-Hexahydro-2,5-dimethyl-3-(phenylmethyl)cyclohept[6,7]imidazo[2,1-b]purin-4(3H)-one: pale yellow foam, FAB MS: M+1=364.

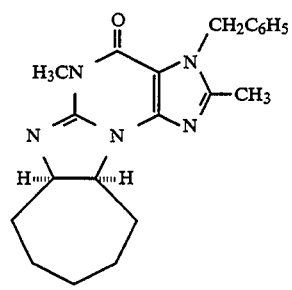

By using 2-(trans-2-hydroxycycloheptylamino)-1,8-dimethyl-7-(phenylmethyl)purin-6-one in accordance with Example 1, the title compound is obtained.

EXAMPLE 15 cis-5,6a,7,8,9,9a-Hexahydro-5-methyl-2-ethyl-3-(phenylmethyl)cyclopent[4,5]imidazo[2,1-b]purin-4(3H)-one: tan solid, EI MS: M+=349.

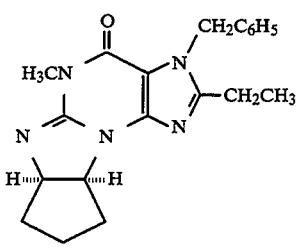

By using 2-(trans-2-hydroxycyclopentylamino)-8-ethyl-1-methyl-7-(phenylmethyl)purin-6-one in accordance with Example 1, the title compound is obtained.

EXAMPLE 16 cis-6a,7,8,9,10,10a-Hexahydro-5-methyl-2-ethyl-3-(phenylmethyl)-3H-benzimidazo[2,1-b]purin-4(5H)-one: pale yellow solid, CI MS: M+1=364.

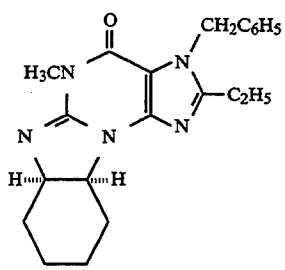

By using 2-(trans-2-hydroxycyclohexylamino )-8-ethyl-1-methyl-7-(phenylmethyl)purin-6-one in accordance with Example 1, the title compound is obtained.

By using the appropriate amino-alcohol in accordance with Example 1, the following compounds are obtained:

16A1 cis-5,6a,7,8,9,9a-Hexahydro-5-methyl-2-ethyl-3-(phenylmethyl)-cyclopent[4,5]imidazo[2,1-b]purin-4(3H)-one: tan solid, EI MS: M+ =349.

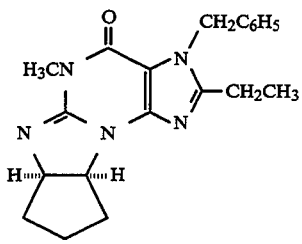

EXAMPLE 17 cis-5,6a,7,8,9,9a-Hexahydro-5-methyl-2-phenyl-3-(phenylmethyl)cyclopent[4,5]imidazo[2,1-b]purin-4(3H)-one: white solid, FAB MS: M+1=398.

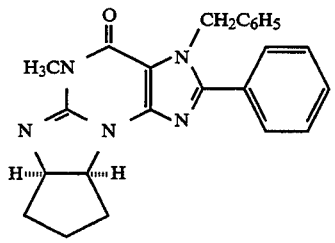

By using 2-(trans-2-hydroxycyclopentylamino )-1-methyl-8-phenyl-7-(phenylmethyl)purin-6-one in accordance with Example 1, the title compound is obtained.

EXAMPLE 17a cis-6a,7,8,9,10,10a-Hexahydro-5-methyl-2-phenyl-3-(phenylmethyl)-3H-benzimidazo[2,1-b]purin-4(5H)-one FAB MS: M+1=412.

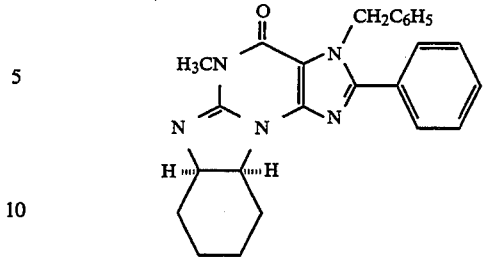

By using 2-(trans-2-hydroxycyclohexylamino)-1-methyl-8-phenyl-7-(phenylmethyl)purin-6-one in accordance with Example 1, the title compound, a white foam, is obtained.

EXAMPLE 18 cis-5,6a,7,8,9,9a-Hexahydro-5-methylcyclopenta[4,5]imidazo[2,1-b]purin-4(3H)-one.

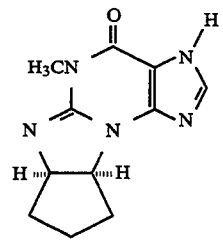

Hydrogenate cis-5,6a,7,8,9,9a-hexahydro-5-methyl-3-(phenylmethyl)cyclopenta[4,5]imidazo[2,1-b]purin-4-one (0.3 g=0.93 mmol) at room temperature/60 psi in EtOH (125 ml) containing 0.4 g Pearlman catalyst. Filter catalyst, remove solvent, and recrystallize to give the title compound as a white solid. FAB MS: M+1=232.

EXAMPLE 19 cis-5,6a,7,8,9,9a-Hexahydro-2,5-dimethylcyclopenta[4,5]imidazo[2,1-b]-purin-4(3H)-one, hydrochloride: white solid, EI MS: M-HCl=245.

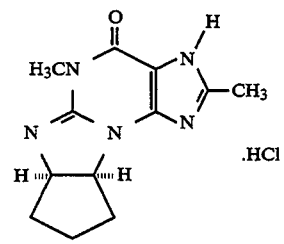

By using cis-5,6a,7,8,9,9a-hexahydro-2,5-dimethyl-3-(phenylmethyl)cyclopent[4,5]imidazo[2,1-b]purin-4(3H)-one in accordance with Example 18, the title compound is obtained.

EXAMPLE 19a cis-5,6a(R),7,8,9,9a(S)-Hexahydro-2,5-di-methylcyclopent[4,5]imidazo[2,1-b]purin-4(3H)-one: white solid, CI MS: M+1=246, $[\alpha]_D^{23.5}$= +153.4°.

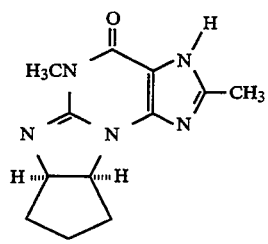

By hydrogenating 5,8a(R),7,8,9,9a(S)-hexahydro-2,5-dimethyl-3-(phenylmethyl)cyclopent[4,5]imidazo[2,1-b]purin-4(3H)-one from Example 10 in accordance with Example 18, the title compound is obtained.

By hydrogenating the corresponding benzyl derivative, the following compounds are obtained in accordance with Example 18.

2′,5′-dimethyl-spiro{cyclopentane-1,7′-(8′H)-(3′H)-imidazo[2,1-b]purin}-4′(5H)-one: white solid, CI MS: M+1=260.

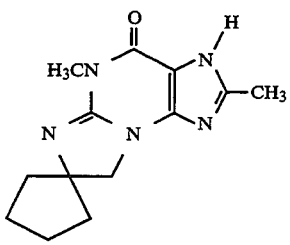

19c 7,8-Dihydro-2,5-dimethyl-7(R)-(1-methylethyl)-3H-imidazo[2,1-b]purin-4(5H)-one: off-white solid, CI MS: M+1=248. $[\alpha]_D^{26} = +84.4°$.

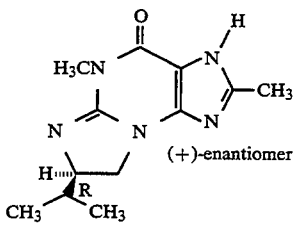

19d 7,8-Dihydro-2,5,7,7-tetramethyl-3H-imidazo[2,1-b]purin-4(5H)-one: white solid, CI MS: M+1=234.

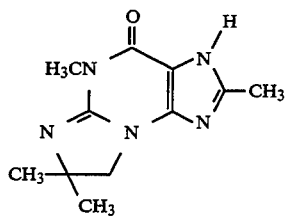

19e 7,8-Dihydro-2,5-dimethyl-7(S)-(1-methylethyl)-3H-imidazo[2,1-b]purin-4(5H)-one: pale yellow solid, CI MS: M+1=248. $[\alpha]_D^{23} = -88.4°$.

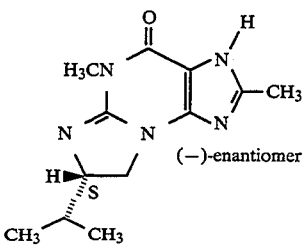

19f 6a(R),7,8,9,10,10a(S)-Hexahydro-2,5-dimethyl-3H-benzimidazo[2,1-b]purin-4(5H)-one: off-white solid, CI MS: M+1=260. $[\alpha]_D^{22} = +116.3°$.

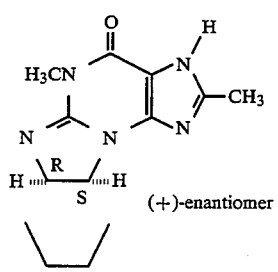

19 g 5′,7′-Dihydro-2′,5′-dimethylspiro{cyclohexane-1,7′(8′H)-imidazo[2,1-b]purin}-4-(3′H)-one: white solid, CI MS: M+1=274.

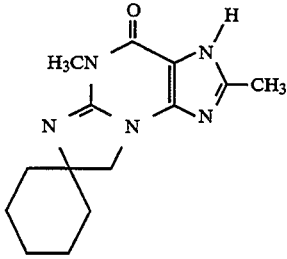

EXAMPLE 20 cis-5,6a,7,8,9,9a-Hexahydro-5-methyl-3-(phenylmethyl)cyclopenta[4,5]imidazo[2,1-b]purin-4(3H)-thione.

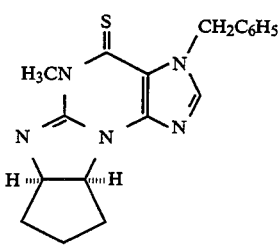

Treat cis-5,6a,7,8,9,9a-hexahydro-5-methyl-3-(phenylmethyl) cyclopenta[4,5]imidazo[2,1-b]purin-4(3H)-one (0.16 g=0.5 mmol) with Lawesson's reagent (0.2 g=0.5 mmol) in xylene overnight. Remove solvent and chromatograph on silica, eluting with 98:2 CH₂Cl₂/MeOH to give the title compound as a yellow foam. FAB MS: M+1=338.

EXAMPLE 20a 5,6a(R),7,8,9,9a(S)-hexahydro-2,5-dimethyl-3-(phenylmethyl)cyclopent[4,5]imidazo[2,1-b]purin-4(3H)-thione FAB MS: M+ =352.

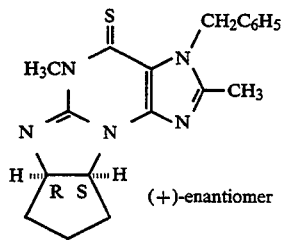

By treating 5,6a(R),7,8,9,9a(S)-hexahydro-2,5-dimethyl-3-(phenylmethyl)cyclopent[4,5]imidazo[2,1-b]purin-4(3H)-one in accordance with Example 20, the title compound is obtained.

EXAMPLE 21 cis-5,6a,7,8,9,9a-Hexahydro-5-methyl-3-(4-chlorophenylmethyl)cyclopenta[4,5]imidazo[2,1-b]purin-4(3H)-one.

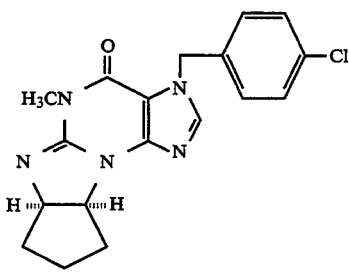

Add a solution of cis-5,6a,7,8,9,9a-hexahydro-5-methylcyclopenta[4,5]imidazo[2,1-b]purin-4-one (0.5 g=2.2 mmol)in DMF drop-wise to a slurry of 60% NaH (0.1 g=2.4 mmol) in DMF at 30° C. When gas evolution ceases, add 4-chlorobenzyl chloride (0.5 g=2.4 mmol) in 2 ml DMF. Heat at 50° C. two hours. Remove DMF and partition between EtOAc and water. Dry, solvent strip, and recrystallize from CH3CN to give the title compound, a white solid. CI MS: M+ =356.

EXAMPLE 22 cis-5,6a,7,8,9,9a-Hexahydro-5-methyl-3-(cyclohexylmethyl)cyclopent[4,5]imidazo[2,1-b]purin-4(3H)-one: off-white foam, FAB MS: M+1=328.

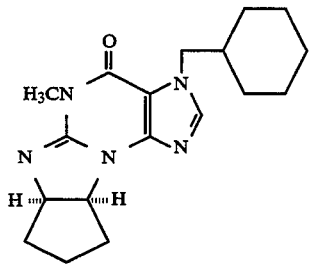

By using bromomethylcyclohexane in accordance with Example 21, the title compound is obtained.

EXAMPLE 23 cis-5,6a,7,8,9,9a-Hexahydro-5-methyl-3-(2-naphthylmethyl)cyclopent[4,5]imidazo[2,1-b]purin-4(3H)-one: white foamed solid, FAB MS: M+1=372.

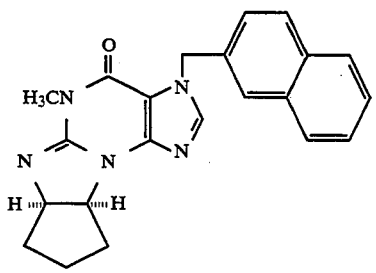

By using 2-(bromomethyl)naphthalene in accordance with Example 21, the title compound is obtained.

By use of the appropriate alkyl halide in accordance with Examples 21-23, the following compounds are obtained:

23A1 5,6a(R),7,8,9,9a(S)-Hexahydro-2,5-dimethyl-3-(4-bromophenylmethyl)cyclopent[4,5]imidazo[2,1-b]purin-4(3H)-one: yellow crystals, EI MS: M+ =414, $[\alpha]_D^{26} = +98.6°$.

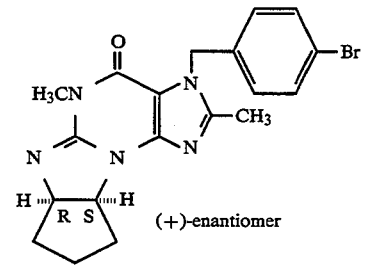

23A2 5,6a(R)-7,8,9,9a(S)-Hexahydro-2,5-dimethyl-3-(4-methoxyphenylmethyl)-cyclopent[4,5]imidazo[2,1-b]purin-4(3H)-one: yellow solid, CI MS: M+1=366, $[\alpha]_D^{26} = +116.7°$.

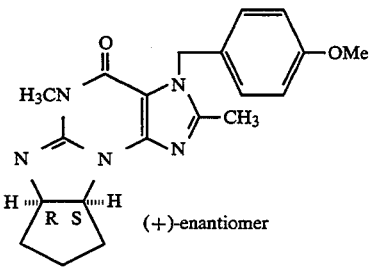

EXAMPLE 24 cis-5,6a,7,8,9,9a-Hexahydro-2,3,5-trimethylcyclopent[4,5]imidazo[2,1-b]purin-4(3H)-one: tan solid, FAB MS: M+1=260.

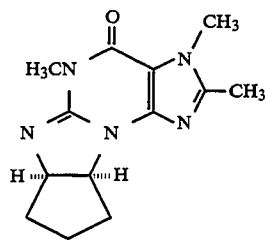

By using cis-5,6a,7,8,9,9a-hexahydro-2,5dimethylcyclopent[4,5]imidazo[2,1-b]purin-4(3H)-one hydrochloride, and methyl iodide instead of 4-chlorobenzyl chloride in accordance with Example 21, the title compound is obtained.

EXAMPLE 25 cis-5,6a,7,8,9,9a-Hexahydro-2-(hydroxymethyl)-5-methyl-3-(phenylmethyl)cyclopent[4,5]imidazo[2,1-b]purin-4(3H)-one

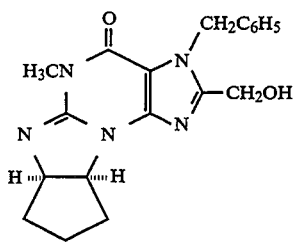

cis-5,6a,7,8,9,9a-Hexahydro-5-methyl-3-(phenylmethyl)cyclopent[4,5]imidazo[2,1-b]purin-4(3H)-one (0.3 gm, 0.93 mmol)in THF (4 ml) is added to a solution of LDA (prepared from diisopropylamine (0.34 ml) in THF (2 ml) and 2.5M n-butyllithium (1.0 ml), at −78° C. After 1 hr at −78° C., formaldehyde is bubbled into the reaction mixture for 10 min.. The mixture is stirred at −78° C. for 30 min., then warmed to room temperature over 30 min. and acetic acid, brine, and CH₂Cl₂ are added. The CH₂Cl₂ layer is concentrated in vacuo and purified by flash chromatography using 5% MeOH in CH₂Cl₂ to give the title compound, a solid, mp 228°-229° C.

EXAMPLE 26 cis-5,6a,7,8,9,9a-Hexahydro-2-methylthio-5-methyl-3-(phenylmethyl)cyclopent[4,5]imidazo[2,1-b]purin-4(3H)-one CI MS: M+1=368.

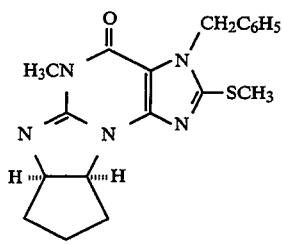

By using LDA and 2.5 eq. CH₃SSCH₃ as the electrophile in accordance with Example 25, the title compound is obtained.

EXAMPLE 27 cis-3,4,5,6a,7,8,9,9a-Octahydro-5-methyl-4-oxo-3-(phenylmethyl)cyclopent[4,5]imidazo[2,1-b]purin-2-carboxylic acid, sodium salt, dihydrate FAB MS: M+1=324.

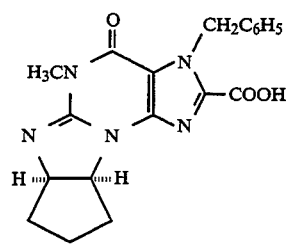

By using LDA and excess carbon dioxide as the electrophile in accordance with Example 25, the title compound is obtained.

EXAMPLE 28 cis-3,4,5,6a,7,8,9,9a-Octahydro-5-methyl-4-oxo-3-(phenylmethyl)cyclopent[4,5]imidazo[2,1-b]purin-2-carboxylic acid, methyl ester, mp 185°-186° C.

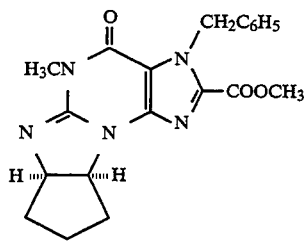

The title compound of Example 27 is treated with ethereal CH₂N₂ to obtain the title compound.

EXAMPLE 29 cis-5,6a,7,8,9,9a-Hexahydro-2-bromo-5-methyl-3-(phenylmethyl)cyclopent[4,5]imidazo[2,1-b]purin-4(3H)one FAB MS: M+1=402, 400.

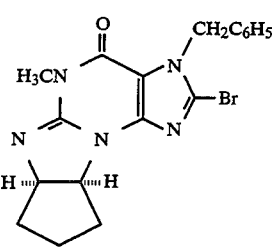

By using 2.5 equivalents (eq) LDA and 2.5 bromine as the electrophile in accordance with Example 25, the title compound is obtained.

EXAMPLE 29a cis-5,6a,7,8,9,9a-Hexahydro-2-(methylaminosulfonyl)-5-methyl-3-(phenylmethyl)cyclopent[4,5]imidazo[2,1-b]purin-4(3H)one

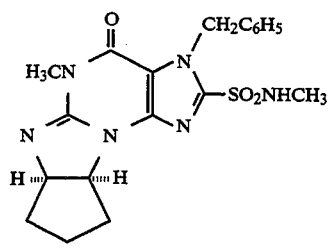

By using LDA, sulfuryl chloride and aqueous methylamine in accordance with Example 25, the title compound is obtained, a solid. EI MS: M=414.

EXAMPLE 30 cis-1-Cyclopentyl-5,6a,7,8,9,9a-hexahydro-5methyl-cyclopent[4,5]imidazo[2,1-b]purin-4(1H)one

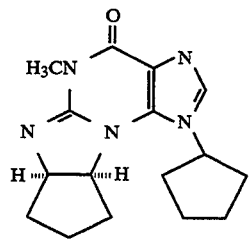

A mixture of 2-bromo-1-methyl-9-cyclopentylpurin-6-one and 2-chloro-1-methyl-9-cyclopentylpurin-6-one (1.4 g) is mixed with (±) trans-2-aminocyclopentanol (1.2 g, 11 mmol) and triethylamine (1.2 ml) in CH₃CN (20 ml) and heated to reflux for 12 hr. The resultant mixture is cooled, concentrated in vacuo, and partitioned between EtOAc/THF 1:1 and brine. The organic layers are concentrated in vacuo and the residue is purified by flash chromatography using 6% EtOH in CH₂Cl₂ to give 2-(trans-2-hydroxycyclopentylamino)-1-methyl-9-cyclopentylpurin-6-one, a solid (1.4 gm, MS FAB: M+H=318). The 2-(trans-2-hydroxy cyclopentylamino )-1-methyl-9-cyclopentylpurin-6-one (1.3 g, 4.1 mm), triphenylphosphine dibromide (prepared from triphenylphosphine (1.2 g) and bromine (0.2 ml)) in DMF (20 ml) is stirred at room temperature for 18 hr and heated to 70° C. for 12 hr. Dilute NaOH is added to the cooled reaction mixture to adjust the pH to 10, and the resultant solution is extracted with EtOAc/THF 1:1. The organic layer is concentrated in vacuo and purified by flash chromatography using 15% EtOH in CH₂Cl₂ and recrystallized from CH₂Cl₂/hexane, to give the title compound, a solid, mp 194°-195° C.

EXAMPLE 31 cis-5,6a,7,8,9,9a-Hexahydro-3,5-bis (phenylmethyl)-cyclopent[4,5]imidazo[2,1-b]purin-4(3H)-one

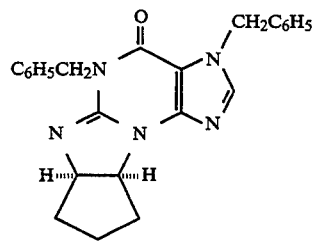

Cyclize 2-(trans-2-hydroxycyclopentylamino)-1,7-bis(phenylmethyl)purin-6-one in accordance with Example 1 to give the title compound, an off-white foamed solid CI MS: M+1=398.

EXAMPLE 32 cis-6a,7,8,9,10,10a-Hexahydro-3,5-bis(phenylmethyl)-3H-benzimidazo[2,1-b]purin-4(5H)one

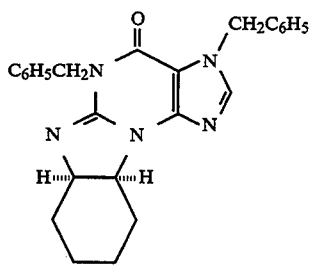

Cyclize 2-(trans-2-hydroxycyclohexylamino)-1,7-bis(phenylmethyl)purin-6-one in accordance with Example 1 to give the title compound, a tan foam, CI MS: M+1=412.

EXAMPLE 33 cis-3-Cyclopentyl-5,6a,7,8,9,9a-hexahydro-5-methyl-cyclopent[4,5]imidazo[2,1-b]purin-4(3H)one

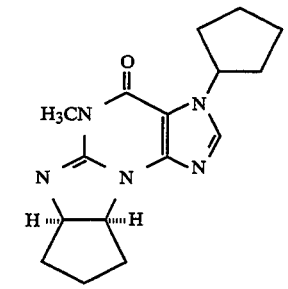

A mixture of 2-bromo-1-methyl-7-cyclopentylpurin-6-one and 2-chloro-1-methyl-7-cyclopentylpurin-6-one (11.4 g), (±) trans-2-aminocyclopentanol (1.2 g, 11 mmol), and triethylamine (1.2 ml) in CH₃CN (20 ml) is heated to reflux for 12 hr. The resultant mixture is cooled, concentrated in vacuo, and partitioned between EtOAc/THF 1:1 and brine. The organic layers are concentrated in vacuo and the residue is purified by flash chromatography using 6% EtOH in CH₂Cl₂ to give 2-(trans-2-hydroxycyclopentylamino)-1-methyl-7-cyclopentylpurin-6-one, a colorless solid (1.4 gm, MS FAB: M+H=318). A mixture of 2-(trans-2-hydroxycyclopentylamino)-1-methyl-7-cyclopentylpurin-6-one (1.3 gm, 4.1 mm) and triphenylphosphine dibromide (prepared from triphenylphosphine (1.2 g) and 0.2 ml bromine) in DMF (20 ml) is stirred at room temperature for 18 hr and heated to 70° C. for 6 hr. Dilute NaOH is added to the cooled reaction mixture to adjust the pH to 10, and the resultant solution is extracted with EtOAC/THF (1:1). The organic layer is concentrated in vacuo and purified by flash chromatography using 15% EtOH in CH2Cl2 and recrystallized from CH2Cl2/hexane to give the title compound, a solid, mp 133°–134° C.

EXAMPLE 34

5'-Methyl-3'-(phenylmethyl)-spiro[cyclopentane-1,7'(8'H)-(3'H)-imidazo[2,1-b]purin]-4'(5'H)one EI MS: M+ =335

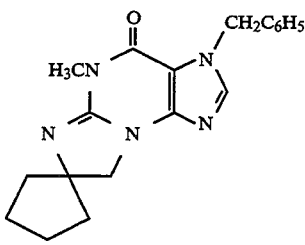

By using 2-(1-hydroxymethylcyclopentylamino)-1-methyl-7-(phenylmethyl)purin-6-one in accordance with Example 1, the title compound, an off-white solid, is obtained.

EXAMPLE 34a

2',5'-Dimethyl-3'-(phenylmethyl)spiro[cyclopentane-1,7'(8'H)-(3'H)-imidazo[2, 1-b]purin]-4'(5'H)one EI MS: M+ =349

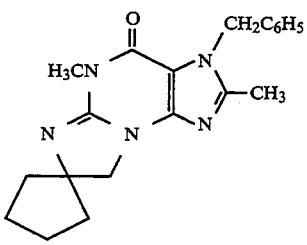

By using 2-(1-hydroxymethylcyclopentylamino)-1,8-dimethyl-7-(phenylmethyl)purin-6-one in accordance with the procedure of Example 1, the title compound, an off-white solid, is obtained.

EXAMPLE 35 cis-5,6a(R),7,8,9,9a(S)-Hexahydro-5-methyl-3-(phenylmethyl)cyclopent[4,5]imidazo[2,1-b]purin-4(3H)one, mp 145°–146° C.

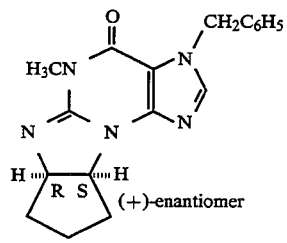

By using 2-(2(R)-hydroxy-1(R)-cyclopentylamino)-1-methyl-7-(phenylmethyl)purin-6-one in accordance with Example 1, the title compound is obtained.

EXAMPLE 36 cis-3-Cyclopentyl-5,6a,7,8,9,9a-hexahydro-2,5-dimethylcyclopent[4,5]imidazo[2,1-b]purin-4(3H)one    CI MS: M+1=314.

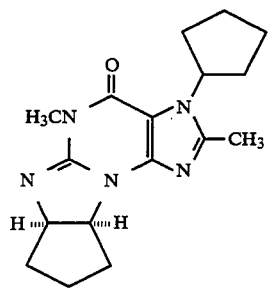

By using cis-3-cyclopentyl-5,6a,7,8,9,9a-hexahydro-5-methylcyclopent[4,5]imidazo[2,1-b]purin-4(3H)one and 2.5 eq. of methyl iodide as the electrophile in accordance with Example 25, the title compound is obtained.

EXAMPLE 37

In accordance with Preparative Example 25, treat the appropriate aminoalcohols with SOCl2 to generate the following cyclic products:

37A1    5'-Methyl-2'-trifluoromethyl-3'-(phenylmethyl)spiro{cyclo-pentane-1,7'(8'H)-(3'H)imidazo[2,1-b]purin}-4'(5'H)-one: white solid, FAB MS: M+ =404.

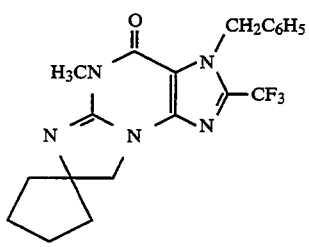

37A2  7,8-Dihydro-5,7,7-trimethyl-2-trifluoromethyl-3-(phenylmethyl)-3H-imidazo[2,1-b]purin-4(5H)-one: white solid, CI MS: M+1=378.

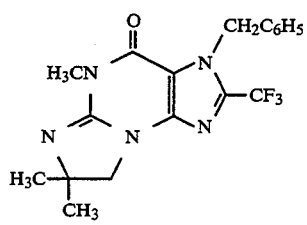

37A3  (+/−)-cis-5,6a,7,8,9,9a-Hexahydro-5-methyl-2-trifluoromethyl-3-(phenylmethyl)cyclopent[4,-5]imidazo[2,1-b]purin-4(3H)-one.

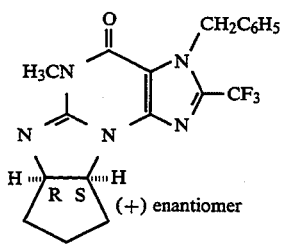

(+) enantiomer

To a solution of the title aminoalcohol of Preparative Example 25 (0.9 g=2.2 mmol) in 40 ml $CH_2Cl_2$ add $SOCl_2$(0.7 ml=9.2 mmol). Stir at room temperature overnight. Wash the diluted solution with cold 2N NaOH, then water. Dry and solvent strip the organic layer. Chromatograph the residue, eluting with 2% $CH_3OH$ in $CH_2Cl_2$ to give the title compound, 0.61 g white solid. CI MS: M+1=390.

EXAMPLE 38

(+,−) 6a,7,8,9,9a,10,11,11a-Octahydro-2,5-dimethyl-3-phenylmethyl)-3H-pentaleno[6a',1':4,5]imidazo[2,1-b]purin-4(5H)-one CI MS: M+1=376

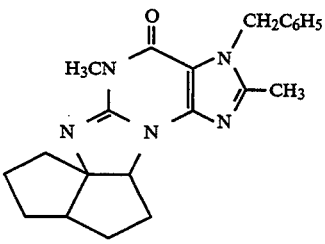

Treat the title compound from Preparative Example 29 with $SOCl_2$ in accordance with Preparative Example 1 to obtain the title compound. The title compound is resolved by HPLC using a chiral stationary phase (Daicel Chiralcel OD) to give the (+) and (−) isomers of the title compound, as described in Examples 39 and 40.

EXAMPLE 39

(+) 6a,7,8,9,9a,10,11,11a-Octahydro-2,5-dimethyl-3-phenylmethyl-3H-pentaleno[6a',1':4,5]imidazo[2,1-b]purin-4(5H)-one CI MS: M+1=376

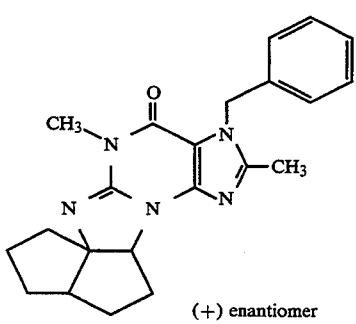

(+) enantiomer

The title compound of Example 38 is resolved by HPLC using a chiral stationary phase (Daicel Chiralcel OD). Elute with 0.1:20:80 diethylamine:2-propanol:hexane to give the title compound as a solid.

EXAMPLE 40

(−)-6a,7,8,9,9a,10,11,11a-Octahydro-2,5-dimethyl-3-phenylmethyl-3H-pentaleno[6a',1':4,5]Imidazo[2,1-b]purin-4(5H)-one CI MS: M+1=376

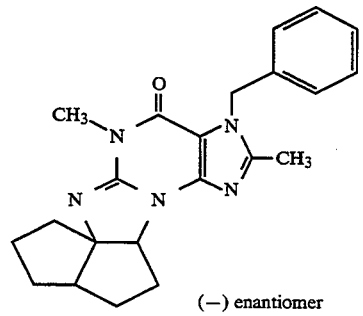

(−) enantiomer

The title compound of Example 38 is resolved by HPLC using a chiral stationary phase (Daicel Chiralcel OD). Elute with 0.1:20:80 diethylamine:2-propanol:hexane to give the title compound as a solid.

EXAMPLE 41

(+/−) 6a,7,8,9,9a,10,11,11a-Octahydro-2,5-dimethyl-3H-pentaleno[6a',1':4,5]imidazo[2,1-b]purin-4(5H)-one, hydrochloride FAB MS: M+1=286

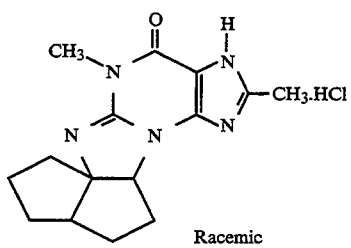

Racemic

Treat the title compound (0.86 g) from Example 38 in EtOH (80 ml) containing conc HCl (0.7 ml) with 20% Pearlman's catalyst (1.0 g) and $H_2$ (60 PSI). After 48 hr, filtered through celite and concentrate to dryness. The residue is dissolved in water and lyophyllized to give the title compound as a colorless powder.

EXAMPLE 41a (+)-6a,7,8,9,9a,10,11,11a-Octahydro-2,5-dimethyl-3H-pentaleno[6a',1':4,5]imidazo[2,1-b]purin-4(5H)-one, hydrochloride $[\alpha]_D$=+114.3 (3 mg/ml EtOH) FAB MS: M+1=286

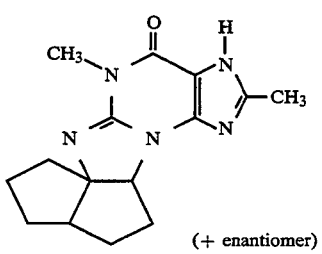

(+ enantiomer)

Treat the title compound from Example 39 in accordance with Example 41 to obtain the title compound as a colorless powder.

EXAMPLE 41b (−)-6a,7,8,9,9a,10,11,11a-Octahydro-2,5-dimethyl-3H-pentaleno[6a',1':4,5]imidazo[2,1-b]purin-4(5H)-one, hydrochloride $[\alpha]_D = -122$ (1.7 mg/ml MeOH) FAB MS: M+1=286

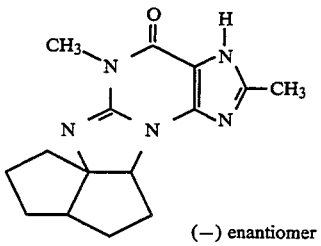

(−) enantiomer

Treat the title compound from Example 40 in accordance with Example 41 to obtain the title compound as a colorless powder.

EXAMPLE 42

(3-Phenylmethyl)-6a,7,8,9,10,10a,11,12,13,13a-decahydro-2,5-dimethyl-napth[1,8a-d]imidazo[2,1-b]purin-4(5H)one EI MS: M+=403

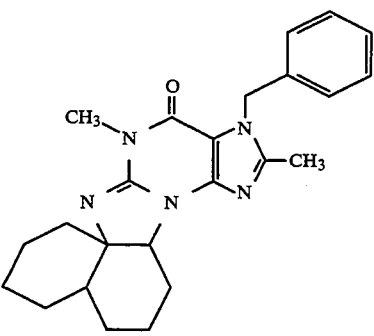

Treat the title compound from Preparative Example 31 with SOCl₂ in accordance with Preparative Example 1 to give the title compound.

EXAMPLE 43

7(R)-cyclohexyl-7,8-dihydro-2,5-dimethyl-3-(phenylmethyl)-3H-imidazo[2,1-b]purin-4(3H)-one solid, CI MS M+1=378

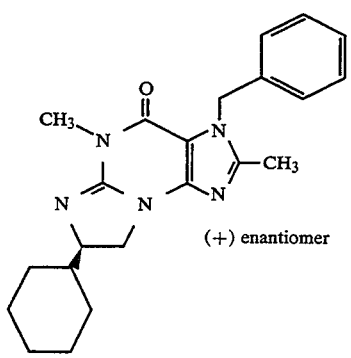

(+) enantiomer

Treat 2-[2-hydroxy-1 (R)-(cyclohexyl)ethylamino]-1-methyl-7-(phenylmethyl)purin-6-one with triphenylphosphine dibromide in DMF at 65° C. for 18 hr. Partition the cooled reaction mixture between water and ethyl acetate. Treat the aqueous phase with dilute sodium hydroxide and extract with ethyl acetate: THF 1:1. Concentrate the organic layer and purify by silica gel chromatography using 6% ethanol in dichloromethane to give the title compound as a beige solid.

EXAMPLE 44

7(R)-cyclohexyl-7,8-dihydro-2,5-dimethyl-3H-imidazo[2,1-b]purin-4(5H)-one hydrochloride: solid, FAB MS M+1=288, $[\alpha]_D^{23} = +46.2°$ (CH₃OH)

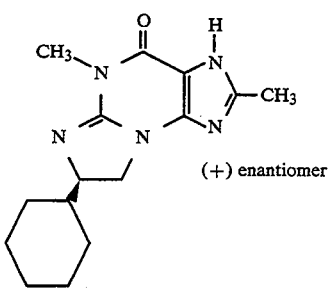

(+) enantiomer

Treat the title compound in Example 43 with Pearlman's catalyst in accordance with Example 41 to give the title compound as a powder.

EXAMPLE 45

7(S)-Cyclohexyl-7,8-dihydro-2,5-dimethyl-3-(Phenylmethyl)-3H-imidazo[2,1-b]purin-4(3H)-one solid, EI MS M+=377, m.p.=99°-101° C.

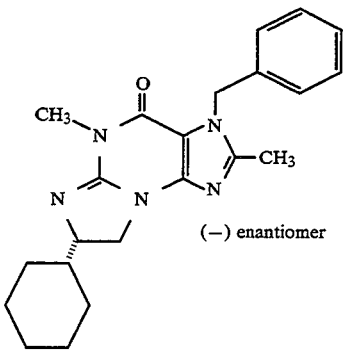

(−) enantiomer

Treat 2-[2-hydroxy-1-(S)-(cyclohexyl)ethylamino]-1-methyl-7-(phenylmethyl)purin-6-one with triphenylphosphine dibromide in accordance with Example 43 to give the title compound as a solid

EXAMPLE 46

7(S)-Cyclohexyl-7,8-dihydro-2,5-dimethyl-3H-imidazo[2,1-b]purin-4(5H)-one hydrochloride: solid, FAB MS M+1=288, $[\alpha]_D^{20.5} = -53.1°$ (CH₃OH)

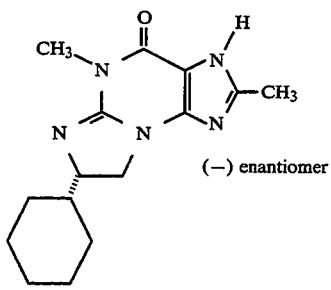

(−) enantiomer

Treat the title compound from Example 45 with Pearlman's catalyst in accordance with Example 41 to give the title compound as a powder.

EXAMPLE 47

5,6a(R),7,8,9,9a(S)-Hexahydro-2,5-dimethyl-3-[(trimethylacetoxy)methyl]-cyclopent[4,5]imidazo[2,1-b]purin-4(3H)-one: solid, FAB MS M+1=360

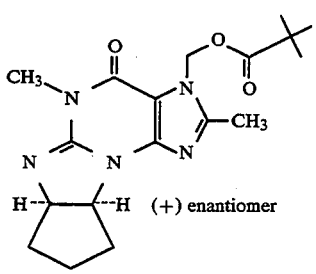

(+) enantiomer

Treat 5,6a(R),7,8,9,9a(S)-hexahydro-2,5-dimethylcyclopent[4,5]imidazo[2,1-b]purin-4(3H)-one from Example 19a (0.28 g, 1.1 mmol) in DMF with (4 ml) with potassium carbonate (0.24 g) and chloromethylpivalate (0.2 ml, 1.4 mmol) at 35° C. for 6 hr. Cool and filter the reaction mixture. Partition the filtrate with brine and ethyl acetate: THF 1:1. Dry and concentrate the organic layer to give the title compound as a powder.

EXAMPLE 48

5,6a(R),7,8,9,9a(S)-Hexahydro-2,5-dimethyl-3-(4-pyridylmethyl)-cyclopent[4,5]imidazo[2,1-b]purin-4(3H)-one: solid, CI MS M+1=337, mp 169°–171° C.

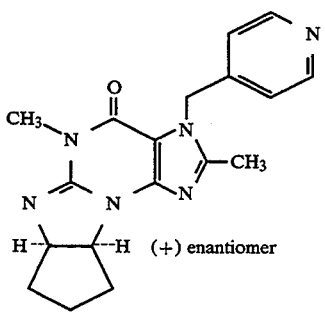

(+) enantiomer

Treat 5,6a(R),7,8,9,9a(S)-hexahydro-2,5-dimethylcyclopent[4,5]imidazo[2,1-b]purin-4(3H)-one from Example 19a with 4-chloromethyl pyridine in accordance with Example 47 to give the title compound as a powder.

EXAMPLE 49

5,6a(R),7,8,9,9a(S)-Hexahydro-2,5-dimethyl-3-[2-(1-morpholinyl)ethyl]cyclopent[4,5]imidazo[2,1-b]purin-4(3H)-one: solid, CI MS M+1=359, mp 144°–145° C.

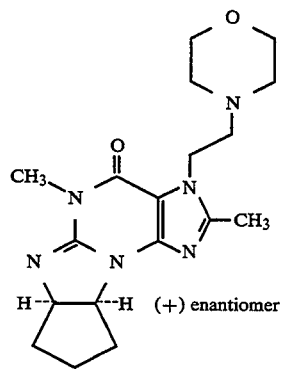

(+) enantiomer

Treat 5,6a(R),7,8,9,9a(S)-hexahydro-2,5-dimethylcyclopent[4,5]imidazo[2,1-b]purin-4(3H)-one from Example 19a with 4-(2-chloroethyl)-morpholine in accordance with Example 47 to give the title compound as a powder.

EXAMPLE 50

5,6a(R),7,8,9,9a(S)-Hexahydro-2,5-dimethyl-3-[acetoxymethyl]cyclopent[4,5]imidazo[2,1-b]purin-4(3H)-one: solid, CI MS M+1=318, mp 144°–145° C.

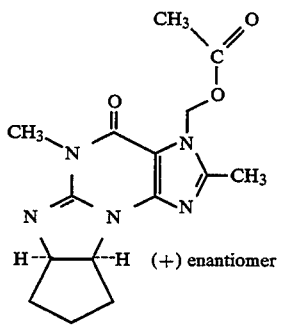

(+) enantiomer

Treat 5,6a(R),7,8,9,9a(S)-hexahydro-2,5-dimethylcyclopent[4,5]imidazo[2,1-b]purin-4(3H)-one from Example 19a with bromomethyl acetate in accordance with Example 47 to give the title compound as a powder.

EXAMPLE 51

5,6a,7,8,9,9a-Hexahydro-2,5,6a-trimethyl-3-(phenylmethyl)cyclopent[4,5]imidazo[2,1-b]purin-4(3H)-one: beige solid, mp 182°–4°.

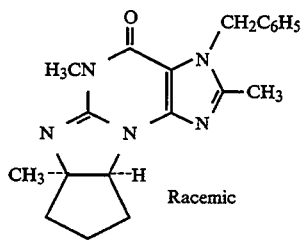

Racemic

By using 2-(2β-hydroxy-1β-methylcyclopentylamino)-1,8-dimethyl-7-(phenylmethyl)purin-6-one in accordance with Example 1, the title compound is obtained.

EXAMPLE 52

5,6a(R),7(S),8,9,9a-Hexahydro-2,5,6a-trimethyl-3-(phenylmethyl)cyclopent[4,5]imidazo[2,1-b]purin-4(3H)-one: yellow solid, mp 193°-5°, $[\alpha]_D^{23} = +38.0°$ (EtOH).

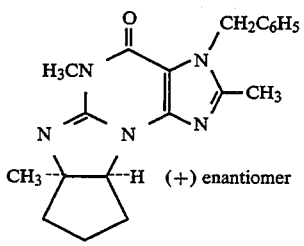

(+) enantiomer

The compound of Example 51 is separated into the individual enantiomers by HPLC (Daicel chiralcel OD, 80:20:0.1 hexane-isopropanol-diethylamine). The (+)-enantiomer is eluted second.

The title compound is also obtained from 2-(2(R)-hydroxy-1(R)-methylcyclopentylamino))-1,8-dimethyl-7-(phenylmethyl)purin-6-one in accordance with Example 1.

EXAMPLE 53

5,6a(S),7(R),8,9,9a-Hexahydro-2,5,6a-trimethyl-3-(phenylmethyl)cyclopent[4,5]imidazo[2,1-b]purin-4(3H)-one]: yellow solid, mp 194°-6°, $[\alpha]_D^{23} = -38.1°$ (EtOH).

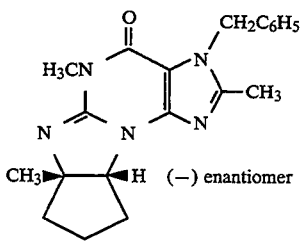

(−) enantiomer

The chiral chromatography described in Example 52 yields the (−)-enantiomer as the first component eluted.

EXAMPLE 54 cis-6a,7,8,9,10,10a-Hexahydro-2,5,7-trimethyl-3-(phenylmethyl)-3H-benzimidazo[2,1-b]purin-4(5H)-one]: tan solid, mp 159°-60°.

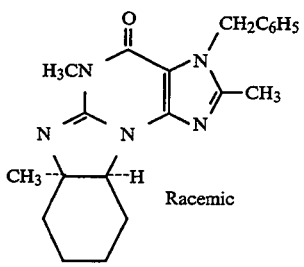

Racemic

By using 2-(2β-hydroxy-1β-methylcyclohexylamino)-1,8-dimethyl-7-(phenylmethyl)purin-6-one in accordance with Example 1, the title compound is obtained.

EXAMPLE 55 cis-5,6a,7,8,9,9a-Hexahydro-2,5,6a-dimethylcyclopent[4,5]imidazo[2,1-b]purin-4(3H)-one]hydrochloride: white solid, FAB MS: M+1=260.

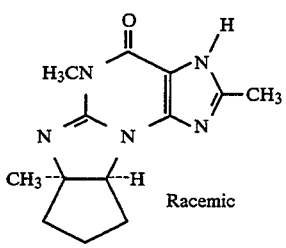

Racemic

By using cis-5,6a,7,8,9,9a-hexahydro-2,5.6a-trimethyl-3-(phenylmethyl)cyclopent[4,5]imidazo[2,1-b]purin-4(3H)-one] in accordance with Example 18, the title compound is obtained.

EXAMPLE 56 cis-6a,7,8,9,10,10a-Hexahydro-2,5,7-trimethyl-3H-benzimidazo[2,1-b]purin-4(5H)-one]: beige solid, mp 262°-4°.

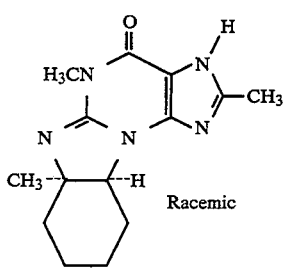

Racemic

By using cis-6a,7,8,9,10,10a-hexahydro-2,5,7-trimethyl-3-(phenylmethyl)-3H-benzimidazo[2,1-b]purin-4(5H)-one in accordance with Example 18, the title compound is obtained.

PREPARATION OF STARTING MATERIALS

The starting materials of formulas (II) and (XX) are well known in the art, as taught, for example, in Weissberger, Pyrimidines, supra and Weissberger, Purines, supra.

The following preparative examples illustrate various methods for preparing starting materials used to make the present invention.

Preparative Example 1

6-Amino-3-methyl-5-(phenylmethyleneamino)pyrimidine-2,4-dione

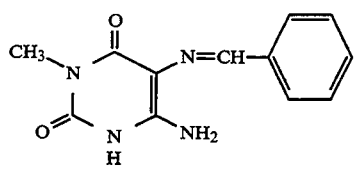

6-amino-3-methyl-5-nitrosopyrimidine-2,4-dione (37.5 g=0.22 mol) with 10% palladium on carbon (Pd/C) (1.9 g) and 25% NaOH (25 ml) in 0.75L water. Hydrogenate at 50 psi for 3 hr, filter through Celite, and dilute to 1.5L with water. Adjust to pH 4.5 with HOAc and add benzaldehyde (35 g=0.34 mol). Add 0.5 kg ice, collect the solid, wash with water, then acetonitrile, and dry to give the title compound as a yellow powder.

Preparative Example 2

6-Amino-3-methyl-5-(phenylmethylamino)pyrimidine-2,4-dione

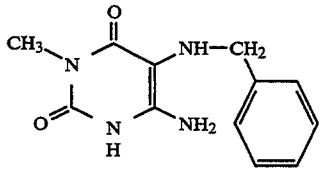

Add 6-amino-3-methyl-5-(phenylmethyleneamino)pyrimidine-2,4-dione (85 g=0.35 mol) to $CH_2Cl_2$ (1.6L) and MeOH (1.6L). Stir the suspension, add HOAc (21.9 ml=0.35 mol), then $NaCNBH_3$ (21.9 g=0.35 mol). Stir 1.5 hr, and add HOAc (2 ml) and $NaCNBH_3$ (2.0 g). After another 30 min, concentrate to ca. 1.6L on a rotovap (35° C. bath). Chill the crystalline mixture, filter, and wash with cold MeOH. Stir the product 15 min in 0.5L boiling MeOH, chill, filter, and dry to obtain the title compound, m.p. 206°–218° C.

Preparative Example 3

1-Methyl-7-(phenylmethyl)purine-2,6-dione

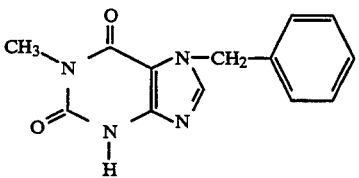

To 6-amino-3-methyl-5-(phenylmethylamino)pyrimidine-2,4-dione (24.6 g=0.1 mol) in DMF (125 ml) at 60° C. add triethyl orthoformate (75 ml=0.45 mol). Heat to 110° C. for 5 hr, cool in ice, filter, and wash with methanol, then ether, to obtain the title compound, m.p. 268°–71° C.

In a similar manner employ the appropriate orthoester to obtain the following 8-substituted products:
3A 1,8-Dimethyl-(7-phenylmethyl)purine-2,6-dione: white solid, m.p. 293°–5° C.
3B 8-Ethyl-1-methyl-7-(phenylmethyl)purine-2,6-dione: pale yellow solid, CI MS: M+1=285.
3C 1-Methyl-8-phenyl-7-(phenylmethyl)purine-2,6-dione: white solid, CI MS: M+1=333.

Preparative Example 4

2-Chloro-1-methyl-7-(phenylmethyl)purin-6-one

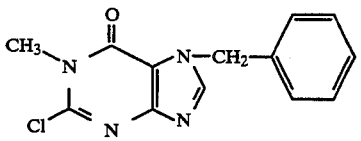

Heat 1-methyl-7-(phenylmethyl)purine-2,6-dione (8.0 g=31 mmol) in $POCl_3$ (80 ml) at reflux 7 hr. Concentrate in vacuo, partition EtOAc-ice water, wash with water, dry and concentrate. Chromatograph on silica with 98:2 $CH_2Cl_2$/MeOH to obtain the title compound as a foam, FAB MS: M+1=275.

Similarly, convert the other materials of Preparative Example 3 into the corresponding chloro-compounds:
4A 2-Chloro-1,8-dimethyl-7-(phenylmethyl)purin-6-one: off-white solid, EI MS: M+1=290.
4B 2-Chloro-8-ethyl-1-methyl-7-(phenylmethyl)purin-6-one: white solid, FAB MS: M+=303.
4C 2-Chloro-1-methyl-8-phenyl-7-(phenylmethyl)purin-6-one: white crystals, CI MS: M+1=351.

Preparative Example 5

2-(trans-2-Hydroxycyclopentylamino)-1-methyl-7-(phenylmethyl)purin-6-one

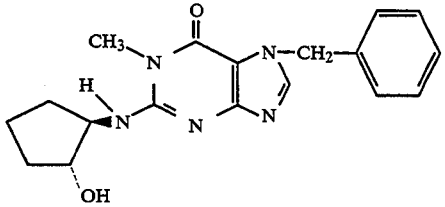

Heat at reflux for 2 days a mixture of 2-chloro-1-methyl-7-(phenylmethyl)purin-6-one (3.14 g=11.4 mmol), triethylamine (1.7 g=16.8 mmol), and (±)-trans-2-aminocyclopentanol (4.04 g=39.9 mmol) in $CH_3CN$ (150 ml). Collect the precipitate, wash with water, and dry to give the title compound, a solid, FAB MS: M+1=340.

Similarly, treat a chloro-compound of Preparative Example 4 with the appropriate amino-alcohol to obtain the following hydroxyalkylamino-purines:
5.1 2-(2-hydroxyethylamino)-1-methyl-7-(phenylmethyl)purin-6-one: white solid, FAB MS: M+1=300.
5.2 2-(trans-2-hydroxycyclohexylamino)-1-methyl-7-(phenylmethyl)purin-6-one: white solid, FAB MS: M+1=354.
5.3 2-(3-hydroxypropylamino)-1-methyl-7-(phenylmethyl)purin-6-one: white solid, FAB MS: M+1=314.
5.4 2-(2-hydroxy-2-phenylethylamino)-1-methyl-7-(phenylmethyl)purin-6-one: white solid, FAB MS: M+1=376.
5.5 2-(1-(hydroxycyclohexyl)methylamino)-1-methyl-7-(phenylmethyl)purin-6-one: white solid, CI MS: M+1=368.
5.6 2-(2-hydroxy-1-indanylamino)-1-methyl-7-(phenylmethyl)purin-6-one: off-white solid, CI MS: M+1=388.
5.7 2-(1-hydroxy-2-indanylamino)-1-methyl-7-(phenylmethyl)purin-6-one: off-white solid, CI MS: M+1=388.
5.8 2-(1-hydroxymethylcyclopentylamino)-1-methyl-7-(phenylmethyl)purin-6-one: white solid, CI MS: M+1=354.
5.9 2-(trans-2-hydroxycyclopentylamino)-1,8-dimethyl-7-(phenylmethyl)purin-6-one: white solid, CI MS: M+1=354.
5.10 (+)-isomer: 2-(2(R)-hydroxy-1(R)-cyclopentylamino)-1,8-dimethyl-7-(phenylmethyl)purin-6-one: white solid, CI MS: M+1=354, $[\alpha]_D^{26}=-8.3°$.
5.11 (−)-isomer: 2-(2(S)-hydroxy-1(S)-cyclopentylamino)-1,8-dimethyl-7-(phenylmethyl)purin-6-one: white solid, EI MS: M+=353, $[\alpha]_D^{26}=-8.2°$.

5A2 2-(trans-2-hydroxycyclohexylamino)-1,8-dimethyl-7-(phenylmethyl)purin-6-one: white solid, CI MS: M+1=368.

5A5 2-(1-(hydroxycyclohexyl)methylamino)-1,8-dimethyl-7-(phenylmethyl)purin-6-one: white solid, CI MS: M+1=382.

5A9 2-(trans-2-hydroxycycloheptylamino )-1,8-dimethyl-7-(phenylmethyl)purin-6-one: white solid, CI MS: M+1=382.

5A10 2-(1-hydroxymethylcyclopentylamino)-1,8-dimethyl-7-(phenylmethyl)purin-6-one: off-white solid, FAB MS: M+1=368.

5A11 2-(1-hydroxy-2-methyl-2-propylamino)-1,8-dimethyl-7-(phenylmethyl)purin-6-one: off-white solid, FAB MS: M+1=341

5A12 2-(1 (R)-phenyl-2-hydroxyethylamino)-1,8-dimethyl-7-(phenylmethyl)purin-6-one: colorless foamed solid, CI MS: M+1=390. $[\alpha]_D^{26}=+29.2°$.

5A13 2-(1-phenyl-3-hydroxy-2(R)-propylamino)-1,8-dimethyl-7-(phenylmethyl)purin-6-one: CI MS: M+1=404. $[\alpha]_D^{26}=+80.1°$.

5A14 2-(1-hydroxy-2(R,S)-butylamino)-1,8-dimethyl-7-(phenylmethyl)purin-6-one: off-white foamed solid. Thin layer chromatography (10% CH3OH in CH2Cl2): one spot, $R_f=0.5$.

5A15 2-((1S,2S)-2-hydroxycyclohexylamino)-8-dimethyl-7-(phenylmethyl)purin-6-one: white foamed solid, CI MS: M+1=368. $[\alpha]_D^{26}=+20.9°$.

5A16 2-((1R,2R)-2-hydroxycyclohexylamino)-1,8-dimethyl-7-(phenylmethyl)purin-6-one: white foam, CI MS: M+=368. $[\alpha]_D^{26}=-21.4°$.

5A17 (+)-isomer: 2-(1-hydroxy-3-methyl-2-butylamino)-1,8-dimethyl-7-(phenylmethyl)purin-6-one: CI MS: M+=356. $[\alpha]_D^{24}=+57°$.

5A18 (−)-isomer: 2-(1-hydroxy-2-propylamino)-1,8-dimethyl-7-(phenylmethyl)purin-6-one: white solid, CI MS: M+=327. $[\alpha]_D^{26}=-1.9°$.

5A19 2-(trans-2-hydroxycyclopentylamino)-1,8-dimethyl-7-(phenylmethyl)purin-6-one: tan solid, EI MS: M+=367.

5A20 (−)-isomer: 2-(1-hydroxy-3-methyl-2-pentylamino)-1,8-dimethyl-7-(phenylmethyl)purin-6-one: white solid, FAB MS: M+1=370. $[\alpha]_D^{26}=-52.1°$.

5A21 (+)-isomer: 2-(1-hydroxy-4-methyl-2-pentylamino)-1,8-dimethyl-7-(phenylmethyl)purin-6-one: white solid, FAB MS: M+1=370. $[\alpha]_D^{26}=+43.7°$.

5A22 2-(1-methoxycarbonyl-2-hydroxyethylamino)-1,8-dimethyl-7-(phenylmethyl)purin-6-one: tan solid, EI MS: M+=371.

5A23 2-(1-hydroxy-2-pentylamino )-1,8-dimethyl-7-(phenylmethyl)purin-6-one: off-white solid, CI MS: M+1=356.

5A24 (−)-isomer: 2-(1-hydroxy-3-methyl-2-butylamino)-1,8-dimethyl-7-(phenylmethyl)purin-6-one: white solid, EI MS: M+=355.

5A25 2-(2-methyl-3-hydroxy-2-butylamino)-1,8-dimethyl-7-(phenylmethyl)purin-6-one: tan foam, CI MS: M+=355.

5A26 2-(2-methyl-4(R,S)-hydroxy-2-pentylamino)-1,8-dimethyl-7-(phenylmethyl)purin-6-one: off-white solid, FAB MS: M+1=370.

5A27 2-[2-hydroxy-1 (R)-(cyclohexyl)ethylamino]-1-methyl-7-(phenylmethyl)purin-6-one, solid $[\alpha]_D^{23.5}=-10.8°$ (CH3OH)

5A28 2-[2-hydroxy-1 (S)-(cyclohexyl)ethylamino]-1-methyl-7-(phenylmethyl)purin-6-one, solid, $[\alpha]_D^{23.5}=+12.1°$ (CH3OH)

5B 2-(trans-2-hydroxycyclopentylamino)-8-ethyl-1-methyl-7-(phenylmethyl)purin-6-one: white solid, CI MS: M+1=368.

5B2 2-(trans-2-hydroxycyclohexylamino)-8-ethyl-1-methyl-7-(phenylmethyl)purin-6-one: white solid, FAB MS: M+1=382.

5C 2-(trans-2-hydroxycyclopentylamino)-1-methyl-8-phenyl-7-(phenylmethyl)purin-6-one: white solid, CI MS: M+1=416.

5C2 2-(trans-2-hydroxycyclohexylamino)-1-methyl-8-phenyl-7-(phenylmethyl)purin-6-one: white solid, FAB MS: M+1=430.

5C3 2-(2(R)-hydroxy-1(R)-cyclopentylamino)-1-methyl-7-(phenylmethyl)purin-6-one; mp 158°–160° C.

Preparative Example 6

6-Amino-3-(phenylmethyl)-2-methylthiopyrimidin-4-(3H)-one

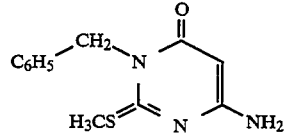

To a slurry of 60% NaH dispersion (1.8 g=45 mmol) in 25 ml DMF at 10° C. add dropwise a solution of 6-amino-2-methylthio-4-hydroxypyrimidine (6.3 g=40 mmol) in 150 ml DMF. When gas evolution subsides, add benzyl bromide (7.5 g=44 mmol). Stir 1.5 hr. at room temperature. Remove DMF and partition the residue between EtOAc and water. Wash the organic layer with water, dry and concentrate. Recrystallize the residue from CH3CN to give the title compound, a white solid. FAB MS: M+1=248.

Preparative Example 7

6-Amino-3-(phenylmethyl)pyrimidine-2,4-dione

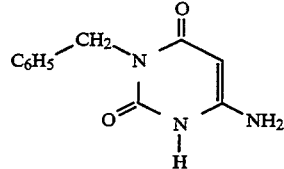

Reflux 6-amino-3-(phenylmethyl)-2-methylthiopyrimidin-4(3H)-one (2.5 g=10 mmol) in 40 ml 10% aqueous NaOH for four hours. Cool, acidify the solution and collect the precipitate. Water wash and dry to give the title compound, a white solid, EI MS: M+=217.

Preparative Example 8

6-Amino-3-(phenylmethyl)-5-nitrosopyrimidine-2,4-dione

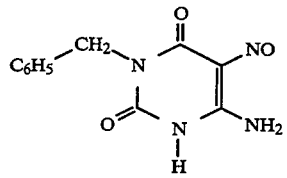

Slurry 6-amino-3-(phenylmethyl)-pyrimidine-2,4-dione (1.1 g=5 mmol) in 50 ml water. Add NaNO$_2$ (0.63 g=9.1 mmol), warm to 75° C. and add acetic acid (2.6 ml=45 mmol) in 30 ml water over two hours. Collect the product, water wash and dry over P$_2$O$_5$ to give title compound as an orange solid. EI MS: M+ =246.

Preparative Example 9

6-Amino-3-(phenylmethyl)-5-(phenylmethyleneamino)-pyrimidine-2,4-dione

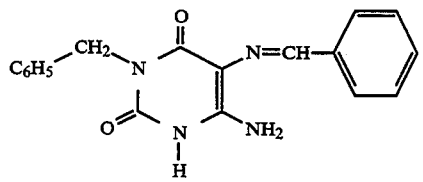

Treat 6-amino-3-(phenylmethyl)-5-nitrosopyrimidine-2,4-dione according to Preparative Example 1 to obtain the title compound, a yellow solid. EI MS: M+ =320.

Preparative Example 10

6-Amino-3-(phenylmethyl)-5-(phenylmethylamino)-pyrimidine-2,4-dione

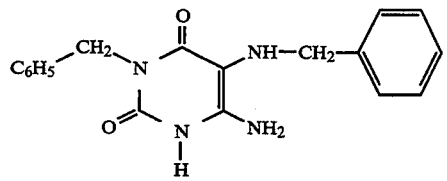

Reduce 6-amino-3-(Phenylmethyl)-5-(phenylmethyleneamino)pyrimidine according the the procedure of Preparative Example 2 to give the title compound, a white solid. CI MS: M+ =322.

Preparative Example 11

1,7-Bis(phenylmethyl)purin-2,6-dione

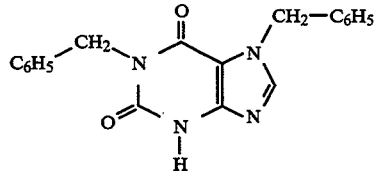

Cyclize 6-amino-3-(phenylmethyl)-5-(phenylmethylamino)pyrimidine-2,4-dione in accordance with Preparative Example 3 to give the title compound, a tan solid. CI MS: M+1=333.

Preparative Example 12

2-chloro-1,7-bis(phenylmethyl)purin-6-one

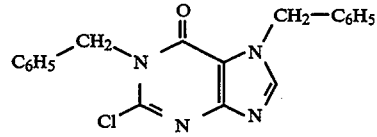

Treat 1,7-bis(phenylmethyl)purin-2,6-dione with POCl$_3$ in accordance with Preparative Example 4, to give the title compound, an off-white solid, EI MS: M+ =350.

Preparative Example 13

2-(trans-2-Hydroxycyclopentylamino)-1,7-bis(phenylmethyl)purin-6-one

Treat 2-chloro-1,7-bis(phenylmethyl)purin-6-one with trans-2-aminocyclopentanol as described in Preparative Example 5 to give the title compound, a tan solid. FAB MS: M+1=416.

Preparative Example 14

2-(trans-2-Hydroxycyclohexylamino)-1,7-bis(phenylmethyl)purin-6-one

Treat 2-chloro-1,7-bis(phenylmethyl)purin-6-one with trans-2-aminocyclohexanol as described in Preparative Example 5 to give the title compound, a tan foam. FAB MS: M+1=430.

Preparative Example 15

2-Chloro-6-benzyloxypurine

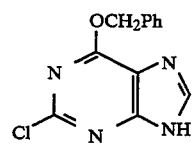

2,6-dichloropurine (0.30 g, 1.6 mmol) is added to a mixture of benzyl alcohol (0.19 g, 1.8 mmol) and 60% sodium hydride (0.13 g, 3.3 mmol) in DMF (8 ml) at room temperature (RT). After 1 hr, the reaction is heated to 60° C. for 18 hr, cooled to RT and dilute HCl is added to adjust the pH to 5. The mixture is extracted with EtOAc/THF 1:1, and the organic layer is dried over sodium sulfate, filtered and concentrated to give a solid. This is recrystallized from EtOAc/hexane to give the title compound, mp. 195°–196° C.

Preparative Example 16

2-Chloro-6-benzyloxy-7-cyclopentylpurine and 2-Chloro-6-benzyloxy-9-cyclopentylpurine

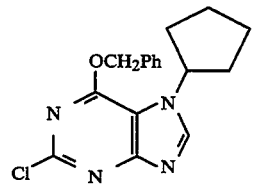

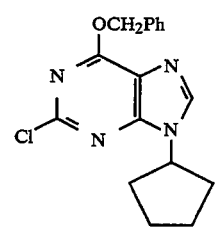

A mixture of 2-chloro-6-benzyloxypurine (0.32 g, 1.2 mmol) cyclopentyl mesylate (0.24 g) and K$_2$CO$_3$ (0.25 g, 1.8 ram)in DMF (10 ml) is heated to 75° C. for 18 hr.

The mixture is cooled to RT and partitioned between brine and EtOAc/THF 1:1. The organic phase is concentrated in vacuo to give a solid, which is purified by flash chromatography. Elution with 40% EtOAc in hexane gives the N-9 isomer of the title compound as a solid FAB MS: M+1=329. Further elution gives the N-7 isomer of the title compound, a solid. FAB MS: M+1=329.

Preparative Example 17

2-Chloro-7-cyclopentylpurin-6-one and
2-Bromo-7-cyclopentylpurin-6-one

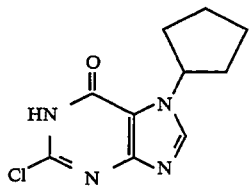

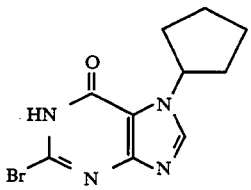

2-Chloro-6-benzyloxy-7-cyclopentylpurine (1.0 g, 3 mmol) is treated with 33% HBr in acetic acid (25 ml). After 1 hr at RT, the mixture is concentrated in vacuo and triturated with H₂O and hexane to give a mixture of the title compounds, a solid. CI MS M+1=285,283 and 241,239.

Preparative Example 18

1-Methyl-2-chloro-7-cyclopentylpurin-6-one and
1-Methyl-2-bromo-7-cyclopentylpurin-6-one

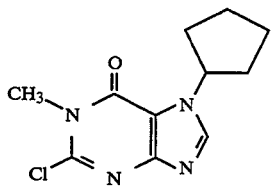

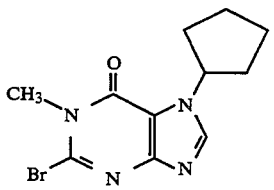

Iodomethane (0.95 ml) is added to a mixture of 2-chloro-7-cyclopentylpurin-6-one and 2-bromo-7-cyclopentylpurin-6-one (1.8 g) and LiOH (0.38 g) in DMF (20 ml) at 0° C. After 1 hr at RT, the mixture is partitioned between EtOAC/THF (1:1), and brine. The organic layers are concentrated in vacuo and the residue is purified by flash chromatography using 3% EtOH in CH₂CL₂ to give a mixture of the title compounds, a solid. mp 140°-145° C.

Preparative Example 19

2-Chloro-9-cyclopentylpurin-6-one and
2-Bromo-9-cyclopentylpurin-6-one

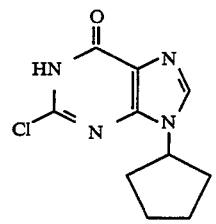

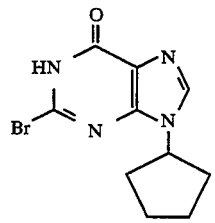

Treat 2-chloro-6-benzyloxy-9-cyclopentylpurine with HBr in acetic acid as described in Preparative Example 17 to give a mixture of the title compounds as a solid. CI MS M+1=285, 283 and 241, 239.

Preparative Example 20

1-Methyl-2-chloro-9-cyclopentylpurin-6-one and
1-methyl-2-bromo-9-cyclopentylpurin-6-one

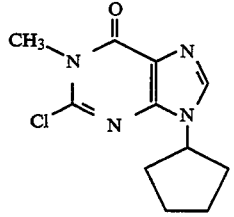

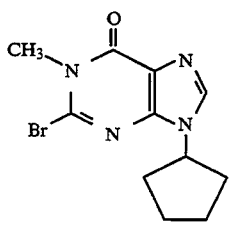

Treat 2-chloro-9-cyclopentylpurin-6-one and 2-bromo-9-cyclopentylpurin-6-one with methyl iodide as described in Preparative Example 18 to give a mixture of the title compounds, a solid. CI MS M+1=299, 297 and 255, 253.

Preparative Example 21

6-Amino-3-methyl-5-(N-(phenylmethyl)tri-fluoracetamido)-pyrimidine-2,4-dione

Add amine from Preparative Example 2 (1.23 g=5 mmol) to a mixture of 1.0 ml trifluoroacetic anhydride and 10 ml trifluoroacetic acid. Reflux overnight. Cool, pour into cold water, collect and water wash the precipitate to give, after drying, 1.45 g of the title compound. One spot on thin layer chromatography; FAB MS: M+=342.

Preparative Example 22

1-Methyl-7-(phenylmethyl)-8-trifluoromethylpurine-2,6-dione

To the trifluoroacetamide (3.4 g=10 mmol) of Preparative Example 21, in 50 ml DMF add sodium methoxide (2.7 g=50 mmol), and heat the mixture, at 130°-150° for 3 hours. Pour into water, acidify, collect and dry the precipitate to give 2.5 g of the title compound, m.p. 211°-213°. CI MS: M+1=325.

Preparative Example 23

2-Chloro-1-methyl-7-(phenylmethyl)-8-trifluoromethylpurin-6-one

Reflux the trifluoromethylpurine of Preparative Example 22 (10.0 g=31 mmol) in 100 ml POCl₃ 10 hours. Remove excess reagent in vacuo, and partition the residue between ice water and ethyl acetate (EtOAc). Wash the the organic layer, dry, and remove solvent. Chromatograph on silica; elute with 2% CH₃OH in CH₂Cl₂ to give 5.1 g of the title compound. Tan solid, CI MS: M+1=343.

Preparative Example 24

(+/−)-2-(trans-2-Hydroxycyclopentylamino)-1-methyl-7-(phenylmethyl)-8-trifluoromethylpurin-6-one Heat under reflux a mixture of the chloropurine of Preparative Example 23 (0 .86 g=2.5 mmol), (+/−)-trans-2-aminocyclopentanol (1.01 g=10 mmol), and triethylamine (0.6 ml=4.3 mmol) in 10 ml CH₃CN overnight. Remove solvent, partition residue between water and EtOAc. Dry the organic layer, remove solvent, and chromatograph the product on silica. Elution with 5% CH₃OH in CH₂Cl₂ gives 0.91 g title compound. Tan foam, FAB MS: M+1=408.

Preparative Example 25

2-(1-hydroxymethylcyclopentylamino)-1-methyl-7-(phenylmethyl)-8-trifluoromethylpurin-6-one: tan foam, CI MS: M+1=422.

Treat the chloropurine of Preparative Example 23 with the appropriate amino alcohol to give the title compound. Similarly prepare:

25.1 2-(1-hydroxy-2-methyl-2-propylamino)-1-methyl-7-(phenylmethyl)-8-trifluoromethylpurin-6-one: white foam, CI MS: M+1=396.

Preparative Example 26

2-[2-(2-Nitrocyclopentyl)ethyl]-1,3-dioxane

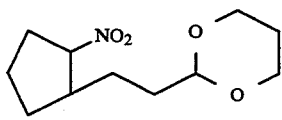

At −78° C., add 1-nitrocyclopentene (1.8 ml, 18.4 mmol) in THF (20 ml) to a THF solution (33 ml) of the zinc-copper reagent prepared from 2-(2-iodoethyl)-1,3-dioxane (5.6 gm, 23 mm), zinc powder (1.58 g), CuCN (1.9 g) and LiCl (1.7 g), according to the general procedure of P. Knochel et. al. (J, Org. Chem. 1989, 54, 5200). After 15 min. warm to 0° C. for one hour, then recool to −78° C. and add AcOH (2.0 ml). Warm to RT, add AcOH:0.1N HCl (15 ml, 1:2) and stir for one hr. Partition between EtOAc and brine. Concentrate the organic layer and purify by silica gel chromatography using EtOAc/Hex 1:3 to elute the title compound (3.6 g 15.7 mmol) as an oil. CI MS: M+1=230.

Preparative Example 27

1-Hydroxy-7-nitrobicyclo[3.3.0]octane

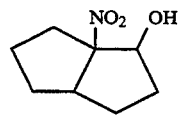

Add toluenesulfonic acid (0.1 g) to a dry MeOH (200 ml) solution of the title compound (3.6 g) from Preparative Example 6. Heat to reflux for 6 hr. then cool to room temperature, add NaHCO₃ (0.1 g) and concentrate to dryness. Dissolve the residue in THF (60 ml) and 0.5N HCl (30 ml). After 13 hr, remove the THF in vacuo and partition the residue with Et₂O and brine. Dry the Et₂O layer (MgSO4), and concentrate. Dissolve the residue (2.0 g) in MeOH (50 ml) and add anhyrdous K₂CO₃ (0.14 g): After seven hours add AcOH (0.15 ml) and concentrate to dryness. Dissolve the residue in Et₂O and wash with brine. Usual workup of the Et₂O layer affords the title compound (2.0 g) CI MS: M+1=172

Preparative Example 28

1-Hydroxy-7-aminobicyclo[3.3.0]octane

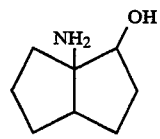

Dissolve the title compound from Example 2 (2.8 g) in EtOH (40 ml), add this to Raney nickel (2 g, wet weight) and place under H₂ at 60 psi. After 48 hr, filter through celite and concentrate the flitrate to dryness. Dissolve the resultant oil (2.7 g) in Et₂O. To this add a solution of dry HCl in MeOH and collect the title compound as a colorless solid. EI MS M+ =141

Preparative Example 29

2-(1-Hydroxybicyclo[3.3.0]octyl-7-amino)-1,8-dimethyl-7-(phenylmethyl)purin-6-one

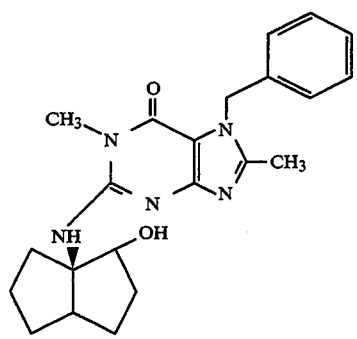

Heat a mixture of the title compound from Preparative Example 28 (10.8 g, 60.8 mmol), 2-chloro-1-methyl-7(phenylmethyl)purin-6-one (21.5 g, 74.4 mmol) and diisopropylethylamine (40 ml) in 1-methyl-2-pyrrolidinone (35 ml) to 140° C. for 64 hr. Cool the mixture and pour into ice water. Collect the resultant precipitate (22 g) and purify this by silica gel chromatography using CH$_2$Cl$_2$: EtOH (90:10) to obtain the title compound (14.2 g) as a solid. CI MS M+1=394.

Preparative Example 30

1-Hydroxy-8a-nitrodecahydronapthalene hydrochloride

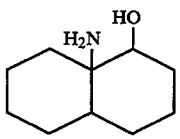

To a solution of 8a-nitrodecahydronapthalen-1-one [P. Dampawan and W. W. Zajac Jr. Synthesis, 545, 1983] (1.2 g, 6.1 mmol) in MeOH (10 ml) at 0° C., add sodium borohydride (0.09 g) and warm to RT. After 0.5 hr, add ether and 1N HCl. Dry and concentrate the organic layer. Dissolve the residue in EtOH (50 ml) and add this to Raney Nickel (1.2 g, wet weight) and place under 60 psi of H$_2$ at 55° C. After 24 hr., filter though celite and concentrate to dryness. Dissolve the resultant oil in Et$_2$O add dry HCl in MeOH and collect the title compound as a colorless precipitate EI MS: M+ =169.

Preparative Example 31

2-(1-Hydroxydecahydronapthalen-8a-ylamino)-1,8-dimethyl-7-(phenylmethyl)purin-6-one: FAB MS: M+1=422

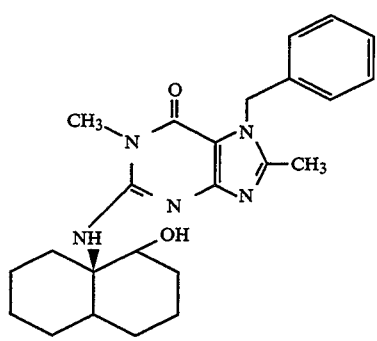

Treat the title compound in Preparative Example 30 with 2-chloro-1,8-dimethyl-7-(phenylmethyl)purin-6-one in accordance with Preparative Example 29 to give the title compound.

Preparative Example 32

2β-Amino-2α-methylcyclopentanol

A. To methyl 1-methyl-2-oxocyclopentanecarboxylate (20.0 g=128 mmol) in THF (800 ml) add portionwise lithium tri-t-butoxyaluminohydride (40.7 g=160 mmol). Stir 1 hr and partition between Et$_2$O and 1.0N HCl. Dry and concentrate to obtain methyl 1-methyl-2-hydroxycyclopentanecarboxylate, largely the 1β-methyl-2β-hydroxy isomer, as an oil.

B. Combine the above ester with 250 ml each 1.0N NaOH and MeOH. After 24 hr, concentrate and partition with EtOAc and 1.0N HCl (saturated with NaCl). Dry and concentrate to obtain 1-methyl-2-hydroxycyclopentanecarboxylic acid, largely the 1β-methyl-2β-hydroxy isomer, as a wet solid.

C. Combine the above acid (5.00 g=34.7 mmol) with Et$_3$N (3.68 g=36.5 mmol) and diphenylphosphoryl azide (10.0 g=36.5 mmol) in toluene (100 ml). Heat at 80° 1 hr, allow to cool, add benzyl alcohol (3.93 g=36.5 mmol), and heat at reflux 18 hr. Allow to cool, concentrate, and partition with EtOAc and 1.0N NaHCO$_3$. Dry and concentrate to obtain an oil. Chromatograph on silica with 1:1 Et$_2$O-hexane to obtain 2α-methyl-2β-(phenylmethoxycarbonylamino)cyclopentanol as an oil.

D. Shake the above carbamate (2.50 g=10.0 mmol) with 10% Pd/C (0.6 g) in MeOH (150 ml) under 60 psi hydrogen. After 2 hr, filter and concentrate to obtain 2β-amino-2α-methylcyclopentanol as an oil.

Preparative Example 33

1(R),2(R)-2-Amino-2-methylcyclopentanol

A. Treat the acid of Preparative Example 32B (10.8 g) in Et$_2$O (110 ml) with (R)-(+)-α-methylbenzylamine (5.42 g)in Et$_2$O (70 ml). Collect the precipitate and dissolve in a boiling mixture of 10:1 CH$_2$Cl$_2$/MeOH (400 ml). Boil down to 200 ml volume, allow to cool, and collect the solid. Recrystallize from CH$_2$Cl$_2$ (60 ml) and MeOH (25 ml) by boiling down with addition of CH$_2$Cl$_2$ (95 ml) to a final volume of 60 ml. Allow to cool and collect the (R)-(+)-α-methylbenzylamine salt of 1(R),2(R)-1-methyl-2-hydroxycyclopentanecarboxylic acid as a solid, mp 172°-30°, $[\alpha]_D^{23}$=−4.90° (EtOH). Partition the salt between Et$_2$O and 1.0N HCl. Dry and concentrate to obtain (R),2(R)-1-methyl-2-hydroxycyclopentanecarboxylic acid as a solid, mp 70°-1°.

B. Treat the above acid in analogous fashion to Preparative Example 32C to obtain 1(R),2(R)-2-methyl-2-(phenylmethoxycarbonylamino)cyclopentanol as an oil.

C. Treat the above carbamate in analogous fashion to Preparative Example 32D to obtain 1(R),2(R)-2-amino-2-methylcyclopentanol as an oil.

Preparative Example 34

2β-Amino-2α-methylcyclohexanol

A. Treat ethyl 1-methyl-2-oxocyclohexanecarboxylate in analogous fashion to Preparative Example 32A to obtain ethyl 1-methyl-2-hydroxycyclohexanecarboxylate, largely the 1β-methyl-2β-hydroxy isomer, as an oil.

B. Combine the above ester (4.97 g=26.7 mmol) with 80 ml each 1.0N NaOH and EtOH. After 48 hr, concentrate and partition with EtOAc and 1.0N HCl (saturated with NaCl). Dry and concentrate to obtain 1-methyl-2-hydroxycyclohexanecarboxylic acid, largely the 1β-methyl-2β-hydroxy isomer, as a beige solid. Recrystallize from Et$_2$O-hexane to obtain the pure isomer as a white solid, mp 97°.

C. Combine the above acid (2.00 g=12.7 mmol) with Et$_3$N (1.40 g=13.9 mmol) and diphenylphosphoryl azide (3.82 g=13.9 mmol) in toluene (40 ml). Heat at 100° 1 hr, allow to cool, and concentrate. Partition with EtOAc and 1.0N NaHCO$_3$, wash with water, dry and concentrate to obtain a solid. Recrystallize from Et$_2$O-hexane to obtain 3aα,4,5,6,7,7aα-hexahydro-3aβ-methyl-2(3H)benzoxazolone as a white solid, mp 107°-9°.

D. Heat the above carbamate (1.10 g=7.09 mmol) with 20% KOH (50 ml) at reflux 4 hr. Allow to cool, saturate with NaCl, and extract with EtOAc. Dry and concentrate to obtain 2β-amino-2α-methylcyclohexanol as a gum.

Preparative Example 35

2-(2β-Hydroxy-1β-methylcyclopentylamino)-1,8-dimethyl-7-(phenylmethyl)purin-6-one Combine the aminoalcohol of Preparative Example 32 (1.10 g=9.6 mmol) and 2-chloro-1,8-dimethyl-7-(phenylmethyl)purin-6-one (2.75=9.6 mmol) with N-methylpyrrolidinone (5.0 g) and diisopropylethylamine (5.2 g). Heat in a sealed vessel at 140° for 40 hr, allow to cool, and partition with EtOAc and water. Dry and concentrate to obtain an oil. Chromatograph on silica with 4% MeOH/CH$_2$Cl$_2$ to obtain the title compound as a foam, FAB MS: M+1=368.

In similar fashion employ the aminoalcohol of Preparative Example 33 to obtain 2-(2(R)-hydroxy-1(R)-methylcyclopentylamino)-1,8-dimethyl-7-(phenylmethyl)purin-6-one as a foam, FAB MS: M+1=368.

In similar fashion employ the aminoalcohol of Preparative Example 34 to obtain 2-(2β-hydroxy-1β-methylcyclohexylamino)-1,8-dimethyl-7-(phenylmethyl)purin-6-one as a foam, FAB MS: M+1=382.

PHARMACEUTICAL PREPARATIONS

The compounds of formulas (I) and (I') can be combined with a suitable pharmaceutical carrier to prepare a pharmaceutical preparation or composition suitable for parenteral or oral administration. Such pharmaceutical compositions are useful in the treatment of cardiovascular and pulmonary disorders such as mammalian hypertension and bronchoconstriction.

The effective daily antihypertensive dose (ED$_{50}$) of the present compounds will typically be in the range of about 1 to about 100 mg/kg of mammalian body weight, administered in single or divided doses. The exact dosage to be administered can be determined by the attending clinician and is dependent upon where the particular compound lies within the above cited range, as well as upon the age, weight and condition of the individual.

Generally, in treating humans in need of treatment for hypertension or bronchoconstriction, the present compounds can be administered in a dosage range of about 10 to about 500 mg per patient generally given a number of times per day, providing a total daily dosage of from about 10 to about 2000 mg per day.

The compositions of the present invention can be administered orally or parenterally. Typical injectable formulations include solutions and suspensions. Typical oral formulations include tablets, capsules syrups, suspensions and elixirs. Also contemplated are mechanical delivery systems, e.g. transdermal dosage forms.

The typical acceptable pharmaceutical carriers for use in the formulations described above are exemplified by sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene glycol polymers; beta-cyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

Following are typical examples of oral and parenteral formulations, wherein the term "Active Ingredient" refers to a compound of formula (I) or (I').

A capsule comprising the Active Ingredient: (+)-6a,7,8,9,9a,10,11,11 a-octahydro-2,5-dimethyl-3H-pentaleno [6a',1':4,5]imidazo[2,1-b]purin-4(5H)-one, hydrochloride is prepared from the following ingredients:

| Capsule | Amount (mg) | |
|---|---|---|
| Active Ingredient | 250.0 | 125.0 |
| Lactose | 173.0 | 86.5 |
| Corn Starch | 75.0 | 37.5 |
| Magnesium Stearate | 2.0 | 1.0 |
| TOTAL | 500.0 | 250.0 |

Blend the active ingredient, lactose and corn starch until uniform; then blend the magnesium stearate into the resulting powder. Encapsulate the mixture into suitably sized two-piece hard gelatin capsules.

| Capsule | Amount (mg) | |
|---|---|---|
| Active Ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| TOTAL | 500.0 | 250.0 |

Blend the active ingredient with the lactose until uniform. Blend the smaller quantity of corn starch with the water and add the resulting corn starch paste then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

| Injectable Solution | mg/ml |
|---|---|
| Active Ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at a temperature of between 60° C.–70° C. and cool the solution to 20° C.–30° C., Charge and dissolve all other excipients and the active ingredient. Bring the solution to final volume, filter it through a sterilizing membrane and fill into sterile containers.

BIOLOGICAL ACTIVITY OF POLYCYCLIC GUANINES

The present compounds are useful in inhibiting the phosphodiesterase enzymes. These phosphodiesterase enzymes are known to hydrolyze cGMP in smooth muscle. High levels of cGMP are associated with the relaxation of vascular smooth muscle, with a consequent subsequent reduction in blood pressure. Thus, it is believed that by inhibiting these phosphodiesterase enzymes, cGMP levels in muscle will be either maintained or increased with a subsequent reduction in blood pressure. In vivo antihypertensive activity is determined orally in spontaneously hypertensive rats (SHR).

Phosphodiesterase Inhibition In Vitro

Compounds are evaluated for inhibition of two phosphodiesterase enzymes which hydrolyze cyclic guanosine monophosphate (cGMP). The first enzyme, calcium-calmodulin dependent phosphodiesterase (CaM-PDE), is a partially pure enzyme obtained from bovine aorta homogenates and purified by DEAE-cellulose and calmodulin-affinity chromatography. The enzyme is activated several fold by Ca-calmodulin and is selective for cGMP, although it will also hydrolyze cAMP. The second enzyme, cGMP phosphodiesterase (cGMP-PDE), is a homogeneous enzyme obtained from bovine lung and purified by ion-exchange chromatography, gel filtration, and sucrose gradient centrifugation. cGMP-PDE is highly selective for cGMP. Bovine aorta homogenates and primary cultures of bovine aortic endothelial and vascular smooth muscle cells contain an enzyme with properties very similar to the lung isozyme.

The enzyme assay is performed using a Biomek Automated Pipetting Station. Compounds are dissolved in distilled water or DMSO and diluted with 10% DMSO. Compounds are tested at several concentrations at log intervals, typically 0.1, 1.0, 10, and 100 $\mu$M final concentration.

Assays contain the following components:
1 $\mu$M substrate $^3$H-cGMP
50 mM Tris-HCl, pH 7.5, 5 mM magnesium chloride (MgCl$_2$)
0.5 mg/ml snake venom alkaline phosphatase
0.1 $\mu$M Calmodulin and 1 mM CaCl$_2$ (for CaM-PDE only)

Assays are initiated by addition of enzyme and stopped by addition of 10 mM isobutylmethylxanthine, a general phosphodiesterase inhibitor. Assays are performed for 25 minutes at room temperature to achieve 5–10% hydrolysis of substrate. The negatively charged substrates are then separated from guanosine by binding to an anion-exchange resin (AG1-X8) and centrifugation or filtration, and the product is quantitated by scintillation counting in counts per minute (cpm) of the remaining soluble material. Percent inhibition is calculated as follows:

% Inhibition = 100 − [(cpm compound-blank)/(cpm control-blank) × 100]

Activity is expresssed as the IC$_{50}$ value, i.e. the concentration required to inhibit activity of enzyme by 50 per cent.

Antihypertensive Activity in Rats

The ability of the compounds of the present invention to lower blood pressure can be assessed in vivo in conscious spontaneously hypertensive rats (SHR). SHR males are purchased from Taconic Farms, Germantown, N.Y. and are approximately 16–18 weeks old when anesthetized with ether. The caudal (ventral tail) artery is cannulated with polyethylene tubing (PE50) and blood pressure and heart rate are recorded as described by Baum, T. et. al, J. Cardiovasc. Pharmacol. Vol 5, pp. 655–667, (1983). Rats are placed into plastic cylindrical cages where they rapidly recover consciousness. Blood pressure and heart rate are allowed to stabilize for approximately 90 minutes prior to compound administration. Compounds are administered orally as solutions or suspensions in 0.4% aqueous methylcellulose vehicle via a feeding needle. The compound or 0.4% aqueous methylcellulose vehicle are given in a volume of 4 ml/kg to SHRs that had been fasted overnight. Activity is expressed as the fall in mean blood pressure (MBP) in millimeters of mercury (mm Hg). Compound-induced changes are compared with the changes in an appropriate placebo group.

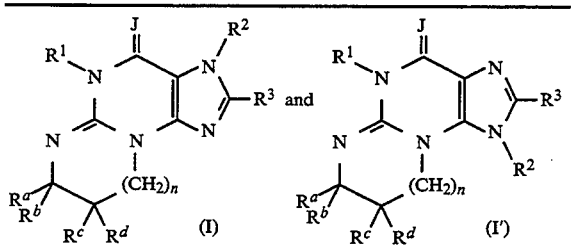

ACTIVITY OF POLYCYLCLIC GUANINES

| Example Number | PDE IC$_{50}$ CaM ($\mu$M) | PDE IC$_{50}$ cGMP ($\mu$M) | SHR Antihypertensive Dose (mpk) | SHR Antihypertensive Fall in MBP (mmHg) |
|---|---|---|---|---|
| 1 | 0.3 | 0.4 | 25 | 30 |
| 3 | 0.1 | 1.4 | 25 | 22 |
| 9 | 0.6 | 0.2 | 25 | 36 |
| 10 | 0.3 | 1.0 | 25 | 45 |
| 12 | 0.2 | 0.2 | 25 | 38 |
| 14 | 0.3 | 0.9 | 25 | 20 |
| 16 | 0.1 | 3 | 25 | 23 |
| 19a | 3.0 | 0.3 | 25 | 40 |
| 20 | 0.04 | 0.4 | 25 | 6 |
| 21 | 3.3 | 0.4 | 25 | 20 |
| 22 | 0.2 | 0.2 | 25 | 15 |
| 28 | 0.2 | 0.2 | 25 | 19 |
| 34 | 0.1 | 0.1 | 25 | 40 |
| 35 | 0.4 | 0.3 | 25 | 41 |
| 34a | 0.3 | 0.8 | 25 | 58 |
| 39 | 0.1 | 0.1 | 25 | 40 |
| 41a | 0.2 | 0.1 | 25 | 67 |
| | | | 10 | 52 |
| | | | 5 | 45 |

We claim:
1. A compound of the formula:

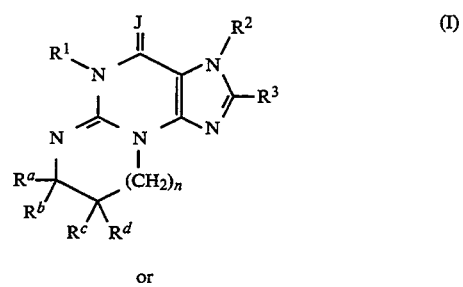

or

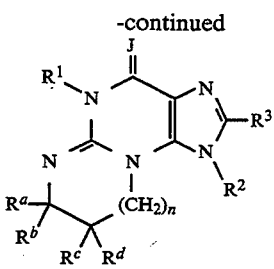

wherein
J is oxygen or sulfur,
R¹ is hydrogen, alkyl or alkyl substituted with aryl or hydroxy;
R² is hydrogen, aryl, heteroaryl, cycloalkyl, alkyl or alkyl substituted with aryl, heteroaryl, hydroxy, alkoxy, amino, monoalkyl amino or dialkylamino, or —(CH$_2$)$_m$TCOR$^{20}$ wherein m is an integer from 1 to 6, T is oxygen or —NH— and R$^{20}$ is hydrogen, aryl, heteroaryl, alkyl or alkyl substituted with aryl or heteroaryl;
R³ is hydrogen, halo, trifluoromethyl, alkoxy, alkylthio, alkyl, cycloalkyl, aryl, aminosulfonyl, amino, monoalkylamino, dialkylamino, hydroxyalkylamino, aminoalkylamino, carboxy, alkoxycarbonyl or aminocarbonyl or alkyl substituted with aryl, hydroxy, alkoxy, amino, monoalkylamino or dialkylamino;
R$^a$, R$^b$, R$^c$ and R$^d$ independently represent hydrogen, alkyl, cycloalkyl or aryl; or (R$^a$ and R$^b$) or (R$^c$ and R$^d$) or (R$^b$ and R$^c$) can complete a saturated ring of 5- to 7-carbon atoms, or (R$^a$ and R$^b$) taken together and (R$^b$ and R$^c$) taken together, each complete a saturated ring of 5- to 7-carbon atoms, wherein each ring optionally can contain a sulfur or oxygen atom and whose carbon atoms may be optionally substituted with one or more or the following: alkenyl, alkynyl, hydroxy, carboxy, alkoxycarbonyl, alkyl or alkyl substituted with hydroxy, carboxy or alkoxycarbonyl; or such saturated ring can have two adjacent carbon atoms which are shared with an adjoining aryl ring; and
n is zero or one.

2. A compound according to claim 1 wherein the compound is of formula (I).

3. A compound according to claim 2 wherein J is O.

4. A compound according to claim 2 wherein R¹ is alkyl, R² is hydrogen, benzyl, 4-chlorobenzyl, trimethylacetoxymethyl or cyclohexylmethyl; and R³ is hydrogen, methyl or ethyl and n is zero.

5. A compound according to claim 2 wherein (R$^a$ and R$^b$) complete a saturated 5 membered ring, (R$^b$ and R$^c$) complete a saturated 5, 6 or 7 membered ring or (R$^a$ and R$^b$) taken together and (R$^b$ and R$^c$) taken together, each complete a saturated ring of 5- to 7-carbon atoms.

6. A compound according to claim 1 which is:
cis-5,6a,7,8,9,9a-Hexahydro-5-methyl-3-(phenylmethyl)cyclopenta[4,5]imidazo[2,1-b]purin-4-one;
7,8-Dihydro-5-methyl-3-(phenylmethyl)-3H-imidazo[2,1-b]purin-4(5H)-one;
cis-6a,7,8,9,10,10a-Hexahydro-5-methyl-3-(phenylmethyl)-3H-benzimidazo[2,1-b]purin-4(5H)-one;
5,7,8,9-Tetrahydro-5-methyl-3-(phenylmethyl)-pyrimido[2,1-b]purin-4(3H)-one;
7,8-Dihydro-8-phenyl-5-methyl-3-(phenylmethyl)-3H-imidazo[2,1-b]purin-4(5H)-one;
5',7'-Dihydro-5'-methyl-3'-(phenylmethyl)spiro[cyclohexane-1,8'-(8H)imidazo[2,1-b]purin]-4'(3'H)-one;
cis-5,6a,11,11a-Tetrahydro-5-methyl-3-(phenylmethyl)indeno[1',2':4,5]imidazo[2,1-b]purin-4(3H)-one;
5',7'-Dihydro-2',5'dimethyl-3'-(phenylmethyl)spiro{cyclohexane-1,7'(8'H)-imidazo[2,1-b]purin}-4'-(3'H)-one;
7,8-Dihydro-2,5,7,7,8(R,S)-pentamethyl-3H-imidazo[2,1-b]purin-4(5H)-one;
cis-5,6a,7,11b-Tetrahydro-5-methyl-3-(phenylmethyl)indeno[2',1',:4,5]imidazo[2,1-b]purin-4(3H)-one;
cis-5,6a,7,8,9,9a-Hexahydro-2,5-dimethyl-3-(phenylmethyl)cyclopent[4,5]imidazo[2,1-b]purin-4-(3H)-one;
5'-Methyl-3'-(phenylmethyl)-spiro[cyclopentane-1,7'-(8'H)-(3'H)imidazo[2,1-b]purin]-4-(5'H)-one;
7,8-Dihydro-2,5,7,7-tetramethyl-3-(phenylmethyl)-3H-imidazo[2,1-b]purin-4(5'H)-one;
7,8-Dihydro-7(R)-phenyl-2,5-dimethyl-3-(phenylmethyl)-3H-imidazo[2,1-b]purin-4(5H)-one;
7,8-Dihydro-2,5-dimethyl-3,7(R)-bis(phenylmethyl)-3H-imidazo[2,1-b]purin-4(5H)-one;
(±)-7,8-Dihydro-2,5-dimethyl-7-ethyl-3-(phenylmethyl)-3H-imidazo[2,1-b]purin-4(5H)-one;
6a(S)-7,8,9,10,10a(R)-Hexhydro-2,5-dimethyl-3-(phenylmethyl)-3H-benzimidazo[2,1-b]purin-4(5H)-one;
6a(R)-7,8,9,10,10a(S)-hexahydro-2,5-dimethyl-3-(phenylmethyl)-3H-benzimidazo[2,1-b]purin-4(5H)-one;
7,8-Dihydro-2,5-dimethyl-7(R)-isopropyl-3-(phenylmethyl)-3H-imidazo[2,1-b]purin-4(5H)-one;
7,8-Dihydro-2,5,7(R)-trimethyl-3-(phenylmethyl)-3H-imidazo[2,1-b]purin-4(5H)-one;
cis-7,7a,8,9,10,10a-Hexahydro-2,5-dimethyl-3-(phenylmethyl)-3H-cyclopenta[5,6]pyrimido[2,1-b]purin-4(5H)-one;
7,8-Dihydro-2,5-dimethyl-7(S)-(1-methylpropyl)-3-(phenylmethyl)-3H-imidazo[2,1-b]purin-4(5H)-one;
7,8-Dihydro-2,5-dimethyl-7(R)-(2-methylpropyl)-3-(phenylmethyl)-3H-imidazo[2,1-b]purin-4(5H)-one;
7,8-Dihydro-2,5-dimethyl-7(R,S)-(methoxycarbonyl)-3-(phenylmethyl)-3H-imidazo[2,1-b]purin-4(5H)-one;
7,8-Dihydro-2,5-dimethyl-7(R,S)-(1-propyl)-3-(phenylmethyl)-3H-imidazo[2,1-b]purin-4(5H)-one;
7,8-Dihydro-2,5-dimethyl-7(S)-(1-methylethyl)-3-(phenylmethyl)-3H-imidazo[2,1-b]purin-4(5H)-one;
7,8-Dihydro-2,5,7,7,8(R,S)-pentamethyl-3H-imidazo[2,1-b]purin-4(5H)-one;
5,7,8,9-Tetrahydro-2,5,7,9(R,S)-pentamethyl-3-(phenylmethyl)-pyrimido[2,1-b]purin-4(3H)-one;
5,6a(R),7,8,9,9a(S)-Hexahydro-2,5-dimethyl-3-(phenylmethyl)cyclopent[4,5]imidazo[2,1-b]purin-4(3H)-one;
5,6a(S),7,8,9,9a(R)-Hexahydro-2,5-dimethyl-3-(phenylmethyl)cyclopent[4,5]imidazo[2,1-b]purin-4(3H)-one;
cis-6a,7,8,9,10,10a-Hexahydro-2,5-dimethyl-3-(phenylmethyl)-3H-benzimidazo[2,1-b]purin-4(5H)-one;
5',7'-Dihydro-2',5'-dimethyl-3'-(phenylmethyl)spiro[cyclohexane-1,8-(8H)-imidazo[2,1-b]purin]-4-(3'H)-one;
cis-5,6a,7,8,9,9a-Hexahydro-2,5-dimethyl-3-(phenylmethyl)cyclohept[6,7]imidazo[2,1-b]purin-4(3H)-one;
cis-5,6a,7,8,9,9a-Hexahydro-5-methyl-2-ethyl-3-(phenylmethyl)cyclopent[4,5]imidazo[2,1-b]purin-4(3H)-one;
cis-6a,7,8,9,10,10a-Hexahydro-5-methyl-2-ethyl-3-(phenylmethyl)-3H-benzimidazo[2,1-b]purin-4-(5H)-one;

cis-5,6a,7,8,9,9a-Hexahydro-5-methyl-2-ethyl-3-(phenylmethyl)cyclopent[4,5]imidazo[2,1-b]purin-4(3H)-one;

cis-5,6a,7,8,9,9a-Hexahydro-5-methyl-2-phenyl-3-(phenylmethyl)cyclopent[4,5]imidazo[2,1-b]purin-4(3H)-one;

cis-6a,7,8,9,10,10a-Hexahydro-5-methyl-2-phenyl-3-(phenylmethyl)-3H-benzimidazo[2,1-b]purin-4(5H)-one;

cis-5,6a,7,8.9,9a-Hexahydro-5-methylcyclopenta[4,-5]imidazo[2,1-b]purin-4(3H)-one;

cis-5,6a,7,8,9,9a-Hexahydro-2,5-dimethylcyclopenta[4,-5]imidazo[2,1-b]purin-4(3H)-one;

cis-5,6a(R), 7,8,9,9a(S)-Hexahydro-2,5-di-methylcyclopent[4,5]imidazo[2,1-b]purin-4(3H)-one;

2',5'-dimethyl-spiro{cyclopentane-1,7'-(8'H)-(3'H)-imidazo[2,1-b]purin}-4'(5'H)-one;

7,8-Dihydro-2,5-dimethyl-7(R)-(1-methylethyl)-3H-imidazo[2,1-b]purin-4(5H)-one;

7,8-Dihydro-2,5,7,7-tetramethyl-3H-imidazo[2,1-b]purin-4(5H)-one;

7,8-Dihydro-2,5-di methyl-7(S)-(1-methylethyl)-3H-imidazo[2,1-b]purin-4(5H)-one;

6a(R),7,8,9,10,10a(S)-Hexahydro-2,5-dimethyl-3H-benzimidazo[2,1-b]purin-4(5H)-one;

5',7'-Dihydro-2',5'-dimethylspiro{cyclohexane-1,7-(8'H)-imidazo[2,1-b]purin}-4'(3'H)-one;

cis-5,6a,7,8,9,9a-Hexahydro-5-methyl-3-(phenylmethyl)cyclopenta[4,5]imidazo[2,1-b]purin-4(3H)-thione;

5,6a(R),7,8,9,9a(S)-Hexahydro-2,5-dimethyl-3-(phenylmethyl)cyclopent[4,5]imidazo[2,1-b]purin-4(3H)-thione;

cis-5,6a,7,8,9,9a-Hexahydro-5-methyl-3-(4-chlorophenylmethyl)cyclopenta[4,5]imidazo[2,1-b]purin-4(3H)-one;

cis-5,6a,7,8,9,9a-Hexahydro-5-methyl-3-(cyclohexylmethyl)cyclopent[4,5]imidazo[2,1-b]purin-4(3H)-one;

cis-5,6a,7,8,9,9a-Hexahydro-5-methyl-3-(2-naphthylmethyl)cyclopent[4,5]imidazo[2,1-b]purin-4(3H)-one;

5,6a(R),7,8,9,9a(S)-Hexahydro-2,5-dimethyl-3-(4-bromophenylmethyl)cyclopent[4,5]imidazo[2,1-b]purin-4(3H)-one;

5,6a(R)-7,8,9,9a(S)-Hexahydro-2,5-dimethyl-3-(4-methoxyphenylmethyl)-cyclopent[4,5]imidazo[2,1-b]purin-4(3H)-one;

cis-5,6a,7,8,9,9a-Hexahydro-2,3,5-trimethylcyclopent[4,5]imidazo[2,1-b]purin-4(3H)-one;

cis-5,6a,7,8,9,9a-Hexahydro-2-(hydroxymethyl)-5-methyl-3-(phenylmethyl)cyclopent[4,5]imidazo[2,1-b]purin-4(3H)-one;

cis-5,6a,7,8,9,9a-Hexahydro-2-methylthio-5-methyl-3-(Phenylmethyl)cyclopent[4,5]imidazo[2,1-b]purin-4(3H)-one;

cis-3,4,5,6a,7,8,9,9a-Octahydro-5-methyl-4-oxo-3-(phenylmethyl)cyclopent[4,5]imidazo[2,1-b]purin-2-carboxylic acid;

cis-3,4,5,6a,7,8,9,9a-Octahydro-5-methyl-4-oxo-3-(phenylmethyl)cyclopent[4,5]imidazo[2,1-b]purin-2-carboxylic acid, methyl ester;

cis-5,6a,7,8,9,9a-Hexahydro-2-bromo-5-methyl-3-(phenylmethyl)cyclopent[4,5]imidazo[2,1-b]purin-4(3H)one;

cis-5,6a,7,8,9,9a-Hexahydro-2-(methylaminosulfonyl)-5-methyl-3-(phenylmethyl)cyclopent[4,-5]imidazo[2,1-b]purin-4(3H)one;

cis-1-Cyclopentyl-5,6a,7,8,9,9a-hexahydro-5-methylcyclopent[4,5]imidazo[2,1-b]purin-4-(1H)one;

cis-5,6a,7,8,9,9a-Hexahydro-3,5-bis-(phenylmethyl)cyclopent(4,5)imidazo(2,1-b)purin-4(3H)one;

cis-6a,7,8,9,10,10a-Hexahydro-3,5-bis-(phenylmethyl)-3H-benzimidazo[2,1-b]purin-4(5H)one;

cis-3-Cyclopentyl-5,6a,7,8,9,9a-hexahydro-5-methylcyclopent[4,5]imidazo(2,1-b)purin-4(3H)one;

5'-Methyl-3'-(phenylmethyl)spiro[cyclopentane-1,7-(8'H)-(3'H)imidazo[2,1-b]purin]-4-(5H)one;

2',5'-Dimethyl-3'-(phenylmethyl)-spiro[cyclopentane-1,7-(8'H)-(3'H)imidazo[2,1-b]purin]-4-(5'H)one;

cis-5,6a,(R)7,8,9,9a(S)-Hexahydro-5-methyl-3-(phenylmethyl)cyclopent[4,5]imidazo(2,1-b)purin-4(3H)one;

cis-3-Cyclopentyl-5,6a,7,8,9,9a-Hexahydro-2,5-dimethylcyclopent[4,5]imidazo[2,1-b]purin-4(3H)one;

5'-Methyl-2'-trifluoromethyl-3'-(phenylmethyl)spiro{cyclo-pentane-1,7'(8'H)-(3'H)imidazo[2,1-b]purin}-4-(5'H)-one;

7,8-Dihydro-5,7,7-trimethyl-2-trifluoromethyl-3-(phenylmethyl)-3H-imidazo[2,1-b]purin-4(5H)-one;

(+/−)-cis-5,6a,7,8,9,9a-Hexahydro-5-methyl-2-trifluoromethyl-3-(phenylmethyl)cyclopent[4,-5]imidazo[2,1-b]purin-4(3H)-one;

(+/−)-6a,7,8,9,9a,10,11,11 a-Octahydro-2,5-dimethyl-3-(phenylmethyl)-3H-pentaleno[6a',1':4,-5]imidazo[2,1-b]purin-4(5H)-one;

(+)-6a,7,8,9,9a,10,11,11a-Octahydro-2,5-dimethyl-3-phenylmethyl-3H-pentaleno[6a',1':4,5]imidazo[2,1-b]purin-4(5H)-one;

(−)-6a,7,8,9,9a,10,11,11a-Octahydro-2,5-dimethyl-3-phenylmethyl-3H-pentaleno[6a',1':4,5]Imidazo[2,1-b]purin-4(5H)-one;

(+/−) 6a,7,8,9,9a,10,11,11a-Octahydro-2,5-dimethyl-3H-pentaleno[6a',1':4,5]imidazo[2,1-b]purin-4(5H)-one;

(+)-6a,7,8,9,9a,10,11,11a-Octahydro-2,5-dimethyl-3H-pentaleno[6a',1':4,5]imidazo[2,1-b]purin-4(5H)-one;

(−)-6a,7,8,9,9a,10,11,11a-Octahydro-2,5-dimethyl-3H-pentaleno[6a',1':4,5]imidazo[2,1-b]purin-4(5H)-one;

6a,7,8,9,10,10a,11,12,13,13a-Decahydro-2,5-dimethyl-(3-phenylmethyl)napth[1,8a-d]imidazo[2,1-b]purin-4(5H)one;

7(R)-Cyclohexyl-7,8-dihydro-2,5-dimethyl-3-(phenylmethyl)-3H-imidazo[2,1-b]purin-4(3H)-one;

7(R)-Cyclohexyl-7,8-dihydro-2,5-dimethyl-3H-imidazo[2,1-b]purin-4(5H)-one;

7(S)-Cyclohexyl-7,8-dihydro-2,5-dimethyl-3-(phenylmethyl)-3H-imidazo[2,1-b]purin-4(3H)-one;

7(S)-Cyclohexyl-7,8-dihydro-2,5-dimethyl-3H-imidazo[2,1-b]purin-4(5H)-one;

5,6a(R),7,8,9,9a(S)-Hexahydro-2,5-dimethyl-3-(trimethylacetoxy)methyl]-cyclopent[4,5]imidazo[2,1-b]purin-4(3H)-one;

5,6a(R),7,8,9,9a(S)-Hexahydro-2,5-dimethyl-3-(4-pyridylmethyl)cyclopent[4,5]imidazo[2,1-b]purin-4(3H)-one;

5,6a(R),7,8,9,9a(S)-Hexahydro-2,5-dimethyl-3-[2-(1-morpholinyl)ethyl]cyclopent[4,5]imidazo[2,1-b]purin-4(3H)-one;

5,6a(R),7,8,9,9a(S)-Hexahydro-2,5-dimethyl-3-[acetoxymethyl]cyclopent[4,5]imidazo[2.1-b]purin-4(3H)-one;

5,6a,7,8,9,9a-Hexahydro-2,5,6a-trimethyl-3-(phenylmethyl)cyclopent[4,5]imidazo[2,1-b]purin-4(3H)-one;

5,6a(R),7(S),8,9,9a-Hexahydro-2,5,6a-trimethyl-3-(phenylmethyl)cyclopent[4,5]imidazo[2,1-b]purin-4(3H)-one;

5,6a(S),7(R),8,9,9a-Hexahydro-2,5,6a-trimethyl-3-(phenylmethyl)cyclopent[4,5]imidazo[2,1-b]purin-4(3H)-one;

cis-6a,7,8,9,10,10a-Hexahydro-2,5,7-trimethyl-3-(phenylmethyl)-3H-benzimidazo[2,1-b]purin-4(5H)-one;

cis-5,6a,7,8,9,9a-Hexahydro-2,5,6a-trimethylcyclopent[4,5]imidazo[2,1-b]purin-4(3H); or cis-6a,7,8,9,10,10a-Hexahydro-2,5,7-trimethyl-3H-benzimidazo[2,1-b]purin-4(5H)-one].

7. A compound according to claim 1 characterized in that

J is O;

$R^1$ is alkyl, $R^2$ is hydrogen, benzyl, 4-chlorobenzyl, cyclohexylmethyl or trimethylacetoxymethyl;

$R^3$ is hydrogen, or alkyl such as methyl or ethyl;

n is zero; and ($R^a$ and $R^b$) form a saturated 5 membered ring, or ($R^b$ and $R^c$) form a saturated 5, 6 or 7 membered ring, or ($R^a$ and $R^b$) and ($R^b$ and $R^c$) each complete a saturated ring and each ring contains 5 or 6 carbon atoms.

8. A compound according to claim 1 which is:

5,6a(R),7,8,9,9a(S)-Hexahydro-2,5-dimethyl-3-(phenylmethyl)cyclopent[4,5]imidazo[2,1-b]purin-4(3H)-one;

5,6a(R),7,8,9,9a(S)-Hexahydro-2,5-dimethylcyclopent[4,5]imidazo[2,1-b]purin-4(3H)-one;

2′,5′-Dimethyl-3′-(phenylmethyl)-spiro[cyclopentane-1,7′-(8′H)-(3′H)imidazo[2,1-b]purin]-4′(5′H)one; or (+)-6a,7,8,9,9a,10,11,11a-Octahydro-2,5-dimethyl-3H-pentaleno[6a′,1′:4,5]imidazo[2,1-b]purin-4(5H)-one.

9. A pharmaceutical composition comprising a compound of formula (I) or (I′) in an amount effective to inhibit phosphodiesterase.

10. A pharmaceutical composition comprising a compound of formula (I) or (I′) in an amount effective to relax smooth muscle.

11. A pharmaceutical composition comprising an anti-hypertensive or a bronchodilating effective amount of the compounds (I) or (I′).

12. A method for treating hypertension or bronchoconstriction in a mammal comprising administering to a mammal in need of such treatment an amount of at least one of compounds (I) or (I′) effective to treat any of the above diseases.

13. A method for maintaining or increasing guanosine 3′:5′-cyclic monophosphate (cGMP) levels in a mammal by administering an amount of compounds (I) or (I′) effective to maintain or increase cGMP.

* * * * *